(12) United States Patent
Gao et al.

(10) Patent No.: US 7,195,885 B2
(45) Date of Patent: Mar. 27, 2007

(54) HEPATITIS C VIRUS ASSAYS

(75) Inventors: Min Gao, Madison, CT (US); Julie A. Lemm, Durham, CT (US); Donald R. O'Boyle, Clinton, CT (US); Peter Nower, Wethersfield, CT (US); Karen Rigat, Clinton, CT (US); Jin-hua Sun, North Haven, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 427 days.

(21) Appl. No.: 10/639,150

(22) Filed: Aug. 12, 2003

(65) Prior Publication Data

US 2004/0121975 A1 Jun. 24, 2004

Related U.S. Application Data

(60) Provisional application No. 60/402,661, filed on Aug. 12, 2002.

(51) Int. Cl.
| | |
|---|---|
| C12Q 1/00 | (2006.01) |
| C12Q 1/70 | (2006.01) |
| C12Q 1/68 | (2006.01) |
| G01N 33/53 | (2006.01) |
| G01N 1/30 | (2006.01) |

(52) U.S. Cl. ................. 435/15; 435/5; 435/6; 435/7.72; 435/40.52

(58) Field of Classification Search ...................... 435/5
See application file for complete search history.

(56) References Cited

U.S. PATENT DOCUMENTS 6,326,137 B1 12/2001 Hong et al.

OTHER PUBLICATIONS

Bartenschlager R & Lohmann V. "Novel cell culture system for the hepatitis C virus" Antiviral Research vol. 52(2001), pp. 1-17.*
Nakayama GR et al "Assessment of alamar blue assay for cellular growth and viability in vitro" J. Immunological Methods vol. 204(1997), pp. 205-208.*
Taliani M. et al. "A continuous assay of hepatitis C virus protease based on resonance energy transfer depsipeptide substrates" Anal. Biochem. vol. 240 (1996), pp. 60-67.*
Bartenschlager, R. et al., "Novel cell culture systems for the hepatitis C virus", Antiviral Research, vol. 52, pp. 1-17 (2001).
Blight, K.J. et al., "Efficient Initiation of HCV RNA Replication in Cell Culture", Science, vol. 290, pp. 1972-1974 (2000).
Collier, J. et al., "Combination Therapy with Interferon-α and Ribavirin for Hepatitis C", BioDrugs, vol. 15, No. 4, pp. 225-238 (2001).

Dymock, B.W., "Emerging therapies for hepatitis C virus infection", Emerging Drugs, vol. 6, No. 1, pp. 13-42 (2001).
Ito, T. et al., "Acquisition of Susceptibility to Hepatitis C Virus Replication HepG2 Cells by Fusion With Primary Human Hepatocytes: Establishment of a Quantitative Assay for Hepatitis C Virus Infectivity in a Cell Culture System", Hepatology, vol. 34, pp. 566-572 (2001).
Lauer, G.M. et al., "Hepatitis C Virus Infection", N. Engl. J. Med., vol. 345, No. 1, pp. 41-52 (2001).
Lohmann, V. et al., "Replication of Subgenomic Hepatitis C Virus RNAs in a Hepatoma Cell Line", Science, vol. 285, pp. 110-113 (1999).
Pietschmann, T. et al., "Characterization of Cell Lines Carrying Self-Replicating Hepatitis C Virus RNAs", Journal of Virology, vol. 75, No. 3, pp. 1252-1264 (2001).
Rodriguez-López, M. et al., "Immunogenicity of variable regions of hepatitis C virus proteins: selection and modification of peptide epitopes to assess hepatitis C virus genotypes by ELISA", Journal of General Virology, vol. 80, pp. 727-738 (1999).
Taliani, M. et al., "A Continuous Assay of Hepatitis C Virus Protease Based on Resonance Energy Transfer Depsipeptide Substrates", Analytical Biochemistry, vol. 240, pp. 60-67 (1996).
Zhang, J.-H. et al., "A Simple Statistical Parameter for Use in Evaluation and Validation of High Throughput Screening Assays", Journal of Biomolecular Screening, vol. 4, No. 2, pp. 67-73 (1999).
Bark, S.J. et al., "Fluorescent Indicators of Peptide Cleavage in the Trafficking Compartments of Living Cells: Peptides Site-Specifically Labeled with Two-Dyes", Methods, vol. 20, No. 4, pp. 429-435 (2000).
Cho, Y.-G. et al., "In vivo assay for hepatitis C viral serine protease activity using a secreted protein", Journal of Virological Methods, vol. 72, No. 1, pp. 109-115 (1998).
Lee, J.K. et al., "*In vitro* cytotoxicity tests on cultured human skin fibroblasts to predict skin irritation potential of surfactants", Toxicology in Vitro, vol. 14, No. 4, pp. 345-349 (2000).

* cited by examiner

*Primary Examiner*—Bruce R. Campell
*Assistant Examiner*—Bo Peng
(74) *Attorney, Agent, or Firm*—Eve L. Frank; Keith R. Lange

(57) ABSTRACT

The present invention includes an assay useful for identifying inhibitors of Hepatitis C virus (HCV) activity. Particularly, the present invention is directed to a dual HCV assay useful for high throughput screening that quantifies both the amount of HCV RNA replication inhibitory activity associated with a test compound and the amount of cytotoxicity associated with that test compound. The present invention also includes compounds discovered using this assay, compositions containing such compounds and methods of treating Hepatitis C by the administration of such compounds. The present invention also includes reporter assays using enzymes associated with HCV RNA replication, as well as a cell line having ATTC Accession No. PTA-4583.

8 Claims, 13 Drawing Sheets

Nucleic Acid Sequence of HCV Replicon: EMBL Accession No. AJ242652

(SEQ ID NO:1)

```
   1 gccagccccc gattgggggc gacactccac catagatcac tccctgtga ggaactactg
  61 tcttcacgca gaaagcgtct agccatggcg ttagtatgag tgtcgtgcag cctccaggac
 121 cccccctccc gggagagcca tagtggtctg cggaaccggt gagtacaccg gaattgccag
 181 gacgaccggg tcctttcttg gatcaacccg ctcaatgcct ggagatttgg gcgtgccccc
 241 gcgagactgc tagccgagta gtgttgggtc gcgaaaggcc ttgtggtact gcctgatagg
 301 gtgcttgcga gtgccccggg aggtctcgta gaccgtgcac catgagcacg aatcctaaac
 361 ctcaaagaaa aaccaaaggg cgcgccatga ttgaacaaga tggattgcac gcaggttctc
 421 cggccgcttg ggtggagagg ctattcggct atgactgggc acaacagaca atcggctgct
 481 ctgatgccgc cgtgttccgg ctgtcagcgc agggcgcccc ggttcttttt gtcaagaccg
 541 acctgtccgg tgccctgaat gaactgcagg acgaggcagc gcggctatcg tggctggcca
 601 cgacgggcgt tccttgcgca gctgtgctcg acgttgtcac tgaagcggga agggactggc
 661 tgctattggg cgaagtgccg gggcaggatc tcctgtcatc tcaccttgct cctgccgaga
 721 aagtatccat catggctgat gcaatgcggc ggctgcatac gcttgatccg gctacctgcc
 781 cattcgacca ccaagcgaaa catcgcatcg agcgagcacg tactcggatg gaagccggtc
 841 ttgtcgatca ggatgatctg gacgaagagc atcaggggct cgcgccagcc gaactgttcg
 901 ccaggctcaa ggcgcgcatg cccgacggcg aggatctcgt cgtgacccat ggcgatgcct
 961 gcttgccgaa tatcatggtg gaaaatggcc gcttttctgg attcatcgac tgtggccggc
1021 tgggtgtggc ggaccgctat caggacatag cgttggctac ccgtgatatt gctgaagagc
1081 ttggcggcga atgggctgac cgcttcctcg tgctttacgg tatcgccgct cccgattcgc
1141 agcgcatcgc cttctatcgc cttcttgacg agttcttctg agtttaaaca gaccacaacg
1201 gtttccctct agcgggatca attccgcccc tctccctccc ccccccctaa cgttactggc
1261 cgaagccgct tggaataagg ccggtgtgcg tttgtctata tgttattttc caccatattg
1321 ccgtcttttg gcaatgtgag ggcccggaaa cctggccctg tcttcttgac gagcattcct
1381 aggggtcttt ccctctcgcc aaaggaatg caaggtctgt tgaatgtcgt gaaggaagca
1441 gttcctctgg aagcttcttg aagacaaaca acgtctgtag cgacccttg caggcagcgg
1501 aaccccccac ctggcgacag tgcctctgc ggccaaaagc cacgtgtata agatacacct
1561 gcaaaggcgg cacaaccca gtgccacgtt gtgagttgga tagttgtgga aagagtcaaa
1621 tggctctcct caagcgtatt caacaagggg ctgaaggatg cccagaaggt acccattgt
1681 atgggatctg atctggggcc tcggtgcaca tgctttacat gtgtttagtc gaggttaaaa
1741 aacgtctagg ccccccgaac cacggggacg tggttttcct ttgaaaaaca cgataatacc
1801 atggcgccta ttacggccta ctcccaacag acgcgaggcc tacttggctg catcatcact
1861 agcctcacag gccgggacag gaaccaggtc gagggggagg tccaagtggt ctccaccgca
1921 acacaatctt cctggcgac ctgcgtcaat ggcgtgtgtt ggactgtcta tcatggtgcc
1981 ggctcaaaga ccttgccgg cccaaagggc caatcaccc aaatgtacac caatgtggac
2041 caggacctcg tcggctggca agcgcccccc ggggcgcgtt ccttgacacc atgcacctgc
2101 ggcagctcgg acctttactt ggtcacgagg catgccgatg tcattccggt gcgccggcgg
2161 ggcgacagca gggggagcct actctccccc aggcccgtct cctacttgaa gggctcttcg
2221 gcggtccac tgctctgccc ctcggggcac gctgtgggca tctttcgggc tgccgtgtgc
2281 acccgagggg ttgcgaaggc ggtggacttt gtacccgtcg agtctatgga accactatg
2341 cggtccccgg tcttcacgga caactcgtcc cctccggccg taccgcagac attccaggtg
```

FIG. 2

2401 gcccatctac acgcccctac tggtagcggc aagagcacta aggtgccggc tgcgtatgca
2461 gcccaagggt ataaggtgct tgtcctgaac ccgtccgtcg ccgccaccct aggtttcggg
2521 gcgtatatgt ctaaggcaca tggtatcgac cctaacatca gaaccggggt aaggaccatc
2581 accacgggtg cccccatcac gtactccacc tatggcaagt ttcttgccga cggtggttgc
2641 tctgggggcg cctatgacat cataatatgt gatgagtgcc actcaactga ctcgaccact
2701 atcctgggca tcggcacagt cctggaccaa gcggagacgg ctggagcgcg actcgtcgtg
2761 ctcgccaccg ctacgcctcc gggatcggtc accgtgccac atccaaacat cgaggaggtg
2821 gctctgtcca gcactggaga aatccccttt tatggcaaag ccatccccat cgagaccatc
2881 aaggggggga ggcacctcat tttctgccat tccaagaaga aatgtgatga gctcgccgcg
2941 aagctgtccg gcctcggact caatgctgta gcatattacc ggggccttga tgtatccgtc
3001 ataccaacta gcggagacgt cattgtcgta gcaacggacg ctctaatgac gggctttacc
3061 ggcgatttcg actcagtgat cgactgcaat acatgtgtca cccagacagt cgacttcagc
3121 ctggacccga ccttcaccat tgagacgacg accgtgccac aagacgcggt gtcacgctcg
3181 cagcggcgag gcaggactgg taggggcagg atgggcattt acaggtttgt gactccagga
3241 gaacggccct cgggcatgtt cgattcctcg gttctgtgcg agtgctatga cgcgggctgt
3301 gcttggtacg agctcacgcc cgccgagacc tcagttaggt tgcgggctta cctaaacaca
3361 ccagggttgc ccgtctgcca ggaccatctg gagttctggg agagcgtctt tacaggcctc
3421 acccacatag acgcccattt cttgtcccag actaagcagg caggagacaa cttcccctac
3481 ctggtagcat accaggctac ggtgtgcgcc agggctcagg ctccacctcc atcgtgggac
3541 caaatgtgga agtgtctcat acggctaaag cctacgctgc acgggccaac gcccctgctg
3601 tataggctgg gagccgttca aaacgaggtt actaccacac accccataac caaatacatc
3661 atggcatgca tgtcggctga cctggaggtc gtcacgagca cctgggtgct ggtaggcgga
3721 gtcctagcag ctctggccgc gtattgcctg acaacaggca gcgtggtcat tgtgggcagg
3781 atcatcttgt ccggaaagcc ggccatcatt cccgacaggg aagtcccttta ccgggagttc
3841 gatgagatgg aagagtgcgc ctcacacctc ccttacatcg aacagggaat gcagctcgcc
3901 gaacaattca aacagaaggc aatcgggttg ctgcaaacag ccaccaagca agcggaggct
3961 gctgctcccg tggtggaatc caagtggcgg accctcgaag ccttctgggc gaagcatatg
4021 tggaatttca tcagcgggat acaatattta gcaggcttgt ccactctgcc tggcaacccc
4081 gcgatagcat cactgatggc attcacagcc tctatcacca gcccgctcac cacccaacat
4141 accctcctgt ttaacatcct gggggggatgg gtggccgccc aacttgctcc tcccagcgct
4201 gcttctgctt tcgtaggcgc cggcatcgct ggagcggctg ttggcagcat aggccttggg
4261 aaggtgcttg tggatatttt ggcaggttat ggagcagggg tggcaggcgc gctcgtggcc
4321 tttaaggtca tgagcggcga gatgccctcc accgaggacc tggttaacct actccctgct
4381 atcctctccc ctggcgccct agtcgtcggg gtcgtgtgcg cagcgatact gcgtcggcac
4441 gtgggcccag gggaggggggc tgtgcagtgg atgaaccggc tgatagcgtt cgcttcgcgg
4501 ggtaaccacg tctcccccac gcactatgtg cctgagagcg acgctgcagc acgtgtcact
4561 cagatcctct ctagtcttac catcactcag ctgctgaaga ggcttcacca gtggatcaac
4621 gaggactgct ccacgccatg ctccggctcg tggctaagag atgtttggga ttggatatgc
4681 acggtgttga ctgatttcaa gacctggctc cagtccaagc tcctgccgcg attgccggga
4741 gtccccttct tctcatgtca acgtgggtac aagggagtct ggcggggcga cggcatcatg
4801 caaaccacct gcccatgtgg agcacagatc accggacatg tgaaaaacgg ttccatgagg
4861 atcgtggggc ctaggacctg tagtaacacg tggcatggaa cattccccat taacgcgtac
4921 accacgggcc cctgcacgcc ctccccggcg ccaaattatt ctagggcgct gtggcgggtg
4981 gctgctgagg agtacgtgga ggttacgcgg gtgggggatt ccactacgt gacgggcatg

FIG. 2 (continued)

```
5041 accactgaca acgtaaagtg cccgtgtcag gttccggccc ccgaattctt cacagaagtg
5101 gatggggtgc ggttgcacag gtacgctcca gcgtgcaaac ccctcctacg ggaggaggtc
5161 acattcctgg tcgggctcaa tcaatacctg gttgggtcac agctcccatg cgagcccgaa
5221 ccggacgtag cagtgctcac ttccatgctc accgacccct cccacattac ggcggagacg
5281 gctaagcgta ggctggccag gggatctccc ccctccttgg ccagctcatc agctagccag
5341 ctgtctgcgc cttccttgaa ggcaacatgc actacccgtc atgactcccc ggacgctgac
5401 ctcatcgagg ccaacctcct gtggcggcag gagatgggcg ggaacatcac ccgcgtggag
5461 tcagaaaata aggtagtaat tttggactct ttcgagccgc tccaagcgga ggaggatgag
5521 agggaagtat ccgttccggc ggagatcctg cggaggtcca ggaaattccc tcgagcgatg
5581 cccatatggg cacgcccgga ttacaaccct ccactgttag agtcctggaa ggacccggac
5641 tacgtccctc cagtggtaca cgggtgtcca ttgccgcctg ccaaggcccc tccgatacca
5701 cctccacgga ggaagaggac ggttgtcctg tcagaatcta ccgtgtcttc tgccttggcg
5761 gagctcgcca caaagacctt cggcagctcc gaatcgtcgg ccgtcgacag cggcacggca
5821 acggcctctc ctgaccagcc ctccgacgac ggcgacgcgg gatccgacgt tgagtcgtac
5881 tcctccatgc cccccttga gggggagccg ggggatcccg atctcagcga cgggtcttgg
5941 tctaccgtaa gcgaggaggc tagtgaggac gtcgtctgct gctcgatgtc ctacacatgg
6001 acaggcgccc tgatcacgcc atgcgctgcg gaggaaacca agctgcccat caatgcactg
6061 agcaactctt tgctccgtca ccacaacttg gtctatgcta caacatctcg cagcgcaagc
6121 ctgcggcaga agaaggtcac ctttgacaga ctgcaggtcc tggacgacca ctaccgggac
6181 gtgctcaagg agatgaaggc gaaggcgtcc acagttaagg ctaaacttct atccgtggag
6241 gaagcctgta agctgacgcc cccacattcg gccagatcta aatttggcta tggggcaaag
6301 gacgtccgga acctatccag caaggccgtt aaccacatcc gctccgtgtg gaaggacttg
6361 ctggaagaca ctgagacacc aattgacacc accatcatgg caaaaaatga ggttttctgc
6421 gtccaaccag agaagggggg ccgcaagcca gctcgcctta tcgtattccc agatttgggg
6481 gttcgtgtgt gcgagaaaat ggcccctttac gatgtggtct ccaccctccc tcaggccgtg
6541 atgggctctt catacggatt ccaatactct cctggacagc gggtcgagtt cctggtgaat
6601 gcctggaaag cgaagaaatg ccctatgggc ttcgcatatg acacccgctg ttttgactca
6661 acggtcactg agaatgacat ccgtgttgag gagtcaatct accaatgttg tgacttggcc
6721 cccgaagcca gacaggccat aaggtcgctc acagagcggc tttacatcgg gggcccctg
6781 actaattcta aagggcagaa ctgcggctat cgccggtgcc gcgcgagcgg tgtactgacg
6841 accagctgcg gtaatacccct cacatgttac ttgaaggccg ctgcggcctg tcgagctgcg
6901 aagctccagg actgcacgat gctcgtatgc ggagacgacc ttgtcgttat ctgtgaaagc
6961 gcggggaccc aagaggacga ggcgagccta cgggccttca cggaggctat gactagatac
7021 tctgccccc ctggggaccc gcccaaacca gaatacgact tggagttgat aacatcatgc
7081 tcctccaatg tgtcagtcgc gcacgatgca tctggcaaaa gggtgtacta tctcacccgt
7141 gaccccacca ccccccttgc gcgggctgcg tgggagacag ctagacacac tccagtcaat
7201 tcctggctag caacatcat catgtatgcg cccaccttgt gggcaaggat gatcctgatg
7261 actcatttct tctccatcct tctagctcag gaacaacttg aaaaagccct agattgtcag
7321 atctacgggg cctgttactc cattgagcca cttgacctac ctcagatcat tcaacgactc
7381 catggcctta gcgcattttc actccatagt tactctccag gtgagatcaa tagggtggct
7441 tcatgcctca ggaaacttgg ggtaccgccc ttgcgagtct ggagacatcg gccagaagt
7501 gtccgcgcta ggctactgtc ccagggggg agggctgcca cttgtggcaa gtacctcttc
7561 aactgggcag taaggaccaa gctcaaactc actccaatcc cggctgcgtc ccagttggat
7621 ttatccagct ggttcgttgc tggttacagc gggggagaca tatatcacag cctgtctcgt
```

FIG. 2 (continued)

7681 gcccgacccc gctggttcat gtggtgccta ctcctactttctgtaggggt aggcatctat
7741 ctactcccca accgatgaac ggggagctaa acactccagg ccaataggcc atcctgtttt
7801 tttcccttt ttttttcttt tttttttttt tttttttttt tttttttttt ttctccttttt
7861 tttttcctct ttttttcctt ttctttcctt tggtggctcc atcttagccc tagtcacggc
7921 tagctgtgaa aggtccgtga gccgcttgac tgcagagagt gctgatactg gcctctctgc
7981 agatcaagt

FIG. 2 (continued)

Amino Acid Sequence of HCV Replicon: EMBL Accession No. AJ242652

(SEQ ID NO:2)

MAPITAYSQQTRGLLGCIITSLTGRDRNQVEGEVQVVSTATQSFLATCVNGVCWTVYHGAGS
KTLAGPKGPITQMYTNVDQDLVGWQAPPGARSLTPCTCGSSDLYLVTRHADVIPVRRRGDSR
GSLLSPRPVSYLKGSSGGPLLCPSGHAVGIFRAAVCTRGVAKAVDFVPVESMETTMRSPVFTD
NSSPPAVPQTFQVAHLHAPTGSGKSTKVPAAYAAQGYKVLVLNPSVAATLGFGAYMSKAHGI
DPNIRTGVRTITTGAPITYSTYGKFLADGGCSGGAYDIIICDECHSTDSTTILGIGTVLDQAETAG
ARLVVLATATPPGSVTVPHPNIEEVALSSTGEIPFYGKAIPIETIKGGRHLIFCHSKKKCDELAAK
LSGLGLNAVAYYRGLDVSVIPTSGDVIVVATDALMTGFTGDFDSVIDCNTCVTQTVDFSLDPT
FTIETTTVPQDAVSRSQRRGRTGRGRMGIYRFVTPGERPSGMFDSSVLCECYDAGCAWYELTP
AETSVRLRAYLNTPGLPVCQDHLEFWESVFTGLTHIDAHFLSQTKQAGDNFPYLVAYQATVC
ARAQAPPPSWDQMWKCLIRLKPTLHGPTPLLYRLGAVQNEVTTTHPITKYIMACMSADLEVV
TSTWVLVGGVLAALAAYCLTTGSVVIVGRIILSGKPAIIPDREVLYREFDEMEECASHLPYIEQG
MQLAEQFKQKAIGLLQTATKQAEAAAPVVESKWRTLEAFWAKHMWNFISGIQYLAGLSTLP
GNPAIASLMAFTASITSPLTTQHTLLFNILGGWVAAQLAPPSAASAFVGAGIAGAAVGSIGLGK
VLVDILAGYGAGVAGALVAFKVMSGEMPSTEDLVNLLPAILSPGALVVGVVCAAILRRHVGP
GEGAVQWMNRLIAFASRGNHVSPTHYVPESDAAARVTQILSSLTITQLLKRLHQWINEDCSTP
CSGSWLRDVWDWICTVLTDFKTWLQSKLLPRLPGVPFFSCQRGYKGVWRGDGIMQTTCPCG
AQITGHVKNGSMRIVGPRTCSNTWHGTFPINAYTTGPCTPSPAPNYSRALWRVAAEEYVEVTR
VGDFHYVTGMTTDNVKCPCQVPAPEFFTEVDGVRLHRYAPACKPLLREEVTFLVGLNQYLVG
SQLPCEPEPDVAVLTSMLTDPSHITAETAKRRLARGSPPSLASSSASQLSAPSLKATCTTRHDSP
DADLIEANLLWRQEMGGNITRVESENKVVILDSFEPLQAEEDEREVSVPAEILRRSRKFPRAMP
IWARPDYNPPLLESWKDPDYVPPVVHGCPLPPAKAPPIPPPRRKRTVVLSESTVSSALAELATK
TFGSSESSAVDSGTATASPDQPSDDGDAGSDVESYSSMPPLEGEPGDPDLSDGSWSTVSEEASE
DVVCCSMSYTWTGALITPCAAEETKLPINALSNSLLRHHNLVYATTSRSASLRQKKVTFDRLQ
VLDDHYRDVLKEMKAKASTVKAKLLSVEEACKLTPPHSARSKFGYGAKDVRNLSSKAVNHI
RSVWKDLLEDTETPIDTTIMAKNEVFCVQPEKGGRKPARLIVFPDLGVRVCEKMALYDVVSTL
PQAVMGSSYGFQYSPGQRVEFLVNAWKAKKCPMGFAYDTRCFDSTVTENDIRVEESIYQCCD
LAPEARQAIRSLTERLYIGGPLTNSKGQNCGYRRCRASGVLTTSCGNTLTCYLKAAAACRAAK
LQDCTMLVCGDDLVVICESAGTQEDEASLRAFTEAMTRYSAPPGDPPKPEYDLELITSCSSNVS
VAHDASGKRVYYLTRDPTTPLARAAWETARHTPVNSWLGNIIMYAPTLWARMILMTHFFSIL
LAQEQLEKALDCQIYGACYSIEPLDLPQIIQRLHGLSAFSLHSYSPGEINRVASCLRKLGVPPLR
VVWRHRARSVRARLLSQGGRAATCGKYLFNWAVRTKLKLTPIPAASQLDLSSWFVAGYSGGDI
YHSLSRARPRWFMWCLLLLSVGVGIYLLPNR

FIG. 3

96-Well Plate Layout

|   | 1 | 2 | 3 | 4 | 5 | 6 | 7 | 8 | 9 | 10 | 11 | 12 |
|---|---|---|---|---|---|---|---|---|---|---|---|---|
| A | Screen | Screen | Screen | Screen | Screen | Screen | Screen | Screen | Screen | Screen | 1-HCV | Inhibited |
| B | Screen | Screen | Screen | Screen | Screen | Screen | Screen | Screen | Screen | Screen | 1-HCV | Inhibited |
| C | Screen | Screen | Screen | Screen | Screen | Screen | Screen | Screen | Screen | Screen | 1-HCV | titration |
| D | Screen | Screen | Screen | Screen | Screen | Screen | Screen | Screen | Screen | Screen | 1-HCV | titration |
| E | Screen | Screen | Screen | Screen | Screen | Screen | Screen | Screen | Screen | Screen | 1-HCV | titration |
| F | Screen | Screen | Screen | Screen | Screen | Screen | Screen | Screen | Screen | Screen | 1-HCV | titration |
| G | Screen | Screen | Screen | Screen | Screen | Screen | Screen | Screen | Screen | Screen | 1-HCV | titration |
| H | Screen | Screen | Screen | Screen | Screen | Screen | Screen | Screen | Screen | Screen | 1-HCV | titration |

FIG. 4

96 hr Treatment with IFN-α

|   | 1 | 2 | 3 | 4 | 5 | 6 | 7 | 8 | 9 | 10 | 11 | 12 |
|---|---|---|---|---|---|---|---|---|---|---|---|---|
| A | 104.23 | 76.73 | 111.73 | 114.03 | 113.13 | 108.83 | 106.93 | 101.23 | 94.93 | 87.63 | 99.83 | -0.75 |
| B | 109.93 | 117.22 | 106.03 | 83.93 | 107.03 | 114.93 | 109.43 | 118.92 | 105.73 | 119.92 | 122.52 | 0.75 |
| C | 119.42 | 121.92 | 111.93 | 99.83 | 114.73 | 115.63 | 116.92 | 116.63 | 107.03 | 60.14 | 109.33 | -0.15 |
| D | 119.62 | 104.03 | 115.13 | 110.23 | 111.83 | 109.03 | 105.73 | 109.83 | 109.03 | 94.73 | 97.53 | 0.45 |
| E | 93.03 | 88.13 | 100.03 | 95.83 | 105.23 | 108.83 | 105.23 | 88.73 | 92.13 | 100.53 | 92.23 | 9.45 |
| F | 110.93 | <u>26.84</u> | 86.83 | 98.83 | 90.23 | 96.43 | 78.53 | 98.83 | 98.13 | 90.73 | 88.23 | 8.75 |
| G | 113.63 | 106.03 | 121.42 | 117.82 | <u>0.85</u> | 116.92 | 99.93 | 107.33 | 116.03 | 102.33 | 90.33 | 44.44 |
| H | 108.83 | 137.02 | 113.83 | 121.72 | 94.93 | 80.33 | 98.13 | 102.23 | 117.52 | 106.63 | 116.63 | 50.44 |

FIG. 7A

|   | 1 | 2 | 3 | 4 | 5 | 6 | 7 | 8 | 9 | 10 | 11 | 12 |
|---|---|---|---|---|---|---|---|---|---|---|---|---|
| A | 0.63 | -2.78 | 5.62 | 5.71 | 8.19 | 1.23 | 4.82 | 1.19 | -1.49 | 3.66 | 2.43 | 16.21 |
| B | 2.89 | 9.86 | 3.88 | -0.49 | 9.26 | 2.84 | 7.55 | 2.11 | 3.84 | 8.28 | 5.97 | 20.64 |
| C | 3.34 | 13.17 | 5.89 | -8.88 | -2.78 | -9.80 | -5.27 | -5.32 | -3.65 | -20.08 | -5.12 | 7.72 |
| D | -1.82 | -2.78 | -0.82 | -2.78 | -8.11 | -5.17 | -8.32 | -8.98 | -13.35 | -5.12 | -5.12 | 14.43 |
| E | 6.06 | -6.01 | 9.18 | 8.62 | 9.18 | 9.09 | 3.93 | 10.20 | -8.98 | 5.40 | 1.83 | 5.09 |
| F | 1.92 | <u>2.75</u> | 9.52 | 12.19 | 5.09 | 11.78 | 3.79 | 9.65 | 8.19 | -2.73 | 1.28 | 6.37 |
| G | 2.84 | 9.18 | 3.20 | 6.06 | <u>82.18</u> | 5.93 | -3.26 | 3.93 | 5.00 | 2.52 | 0.02 | 6.19 |
| H | 1.23 | 3.56 | 2.70 | -2.44 | 1.46 | -3.70 | 2.98 | 6.02 | 2.65 | 1.28 | -1.30 | 0.63 |

FIG. 7B

HEPATITIS C VIRUS ASSAYS

RELATED APPLICATIONS

This application claims the benefit under 35 U.S.C. Section 119(e) of U.S. Provisional Patent Application No. 60/402,661 filed Aug. 12, 2002.

FIELD OF THE INVENTION

The present invention includes assays useful for identifying inhibitors of Hepatitis C virus (HCV) activity. Particularly, the present invention includes a dual HCV assay useful for high throughput screening that quantifies both the amount of HCV RNA replication inhibitory activity associated with a test compound and the amount of cytotoxicity associated with the test compound. As such, an assay of the present invention permits the determination of both inhibitory activity associated with a test compound and selectivity of that test compound in a single well. The present invention also includes a reporter assay utilizing at least one enzyme associated with HCV RNA replication. The present invention also includes a cell line useful in assay of the present invention.

BACKGROUND OF THE INVENTION

Hepatitis C virus (HCV) is the major etiological agent of 90% of all cases of non-A, non-B hepatitis (Dymock, B. W. *Emerging Drugs* 6:13–42 (2001)). The incidence of HCV infection is becoming an increasingly severe public health concern with 2–15% individuals infected worldwide. While primary infection with HCV is often asymptomatic, most HCV infections progress to a chronic state that can persist for decades. Of those with chronic HCV infections, it is believed that about 20–50% will eventually develop chronic liver disease (e.g. cirrhosis) and 20–30% of these cases will lead to liver failure or liver cancer. As the current HCV-infected population ages, the morbidity and mortality associated with HCV are expected to triple.

Known treatments for HCV infection include the use of interferon-α (IFN), which indirectly effects HCV infection by stimulating the host antiviral response. IFN treatment is largely ineffective, however, as a sustained antiviral response is produced in less than 30% of treated patients. Further, IFN treatment induces an array of side effects of varying severity in upwards of 90% of patients (e.g. acute pancreatitis, depression, retinopathy, thyroiditis). Therapy with a combination of IFN and ribavirin has provided a slightly higher sustained response rate, but has not alleviated the IFN-induced side effects.

One research area of active interest includes the development of antiviral agents which inactivate virally encoded protein products essential for HCV viral replication. Examples of such agents include various tripeptide compounds, which act as selective HCV NS3 serine protease inhibitors. However, many of these compounds do not sufficiently inhibit HCV protease activity or do not have sufficient potency, and thus, may not provide optimal treatment of HCV-infected patients. Accordingly, there is an ongoing need for the development of HCV assays for the identification of agents effective for inactivating viral replication proteins.

Known cell-based assays for screening compounds for HCV inhibitory activity rely upon the detection of viral RNA replication using RT-PCR (Ito et al., *Hepatology* 34(3): 566–572 (2001); Bartenschlager R. and V. Lohman, *Antiviral Res.* 52(1):1–17 (2001)). Such cell-based systems often yield variable results, making reproducibility a major problem and the use of such system for the screening of compounds impractical, particularly for use in high throughput screening (HTS). HCV assays which rely on the inhibition of viral enzymes essential for viral replication and which may be suitable for HTS are known (Bianchi et al., *Analytical Biochemistry* 237, 239–244 (1996); Taliani et al., *Analytical Biochemistry* 240, 60–67 (1996)), but such assays measure only in vitro activity.

Accordingly, there exists a need for an accurate and reproducible cell-based HCV assays which permits the screening of compounds for HCV replication inhibitory activity. The present invention is directed towards such assays.

SUMMARY OF THE INVENTION

The present invention includes a cell-based HCV assay which measures the inhibitory activity of compounds on HCV RNA replication. The present invention may include a dual assay useful for high throughput screening that quantifies both: (i) the amount of HCV RNA replication inhibitory activity associated with a test compound; and (ii) the amount of cytotoxicity associated with the test compound. Desirably, both steps are conducted in a single well. Assays of the present invention permit the determination of both the inhibitory activity as well as the selectivity of a test compound in a HTS.

In one aspect, the present invention includes an assay for identifying a compound that inhibits HCV RNA replication. The assay comprising the steps of: (a) providing a cell which expresses at least one enzyme associated with HCV RNA replication; (b) contacting the cell with a test compound; (c) determining whether the test compound inhibits HCV RNA replication; and (d) determining whether the test compound is cytotoxic to the cell. The cell expressing at least one enzyme associated with HCV RNA replication may include a HCV replicon which is a polynucleotide having the nucleic acid sequence set forth in SEQ ID NO:1 and encoding a polypeptide having the amino acid sequence set forth in SEQ ID NO:2. Further, the HCV replicon may be the molecular construct set forth in FIG. 1. A cell useful in the present invention has the ATTC Accession No. PTA-4583.

Both steps of an assay of the present invention are desirably conducted in a single well, or may be conducted in two or more wells. The enzyme associated with HCV RNA replication may be any enzyme associated with HCV RNA replication, and is desirably a protease, such as a serine protease. The serine protease is desirably NS3 protease. The protein may also be NS4A. The step of determining whether the test compound inhibits HCV RNA replication is desirably conducted by contacting the cell with a fluorescence substrate, and the step of determining whether the test compound is cytotoxic to the cell is desirably conducted by contacting the cell with an Alamar Blue solution.

The present invention also includes compounds and pharmaceutical compositions containing such compounds identified by the inventive assay. Further, the present invention includes a method for treating hepatitis-C by administering to a mammalian species in need thereof a therapeutically effective amount of such a compound.

In another aspect, the present invention includes an assay for identifying a compound that inhibits HCV RNA replication, which comprises the steps of: (a) providing a cell which expresses at least one enzyme associated with HCV RNA replication; (b) contacting the cell with a test compound; (c) contacting the cell with a compound which permits the determination of whether the test compound inhibits HCV RNA replication; and (d) contacting the cell with an indicator solution which permits the determination of whether the test compound is cytotoxic to the cell. The compound which permits the determination of whether the test compound inhibits HCV RNA replication is desirably a FRET peptide, and the indicator solution which permits the determination of whether the test compound is cytotoxic to the cell is desirably an Alamar Blue solution.

In another aspect, the present invention includes an assay for identifying a compound that inhibits HCV RNA replication. The assay comprises the steps of: (a) providing a cell which expresses at least one enzyme associated with HCV RNA replication, the cell comprising a HCV replicon; (b) contacting the cell with a test compound; (c) contacting the cell with a FRET peptide for determining whether the test compound inhibits HCV RNA replication; and (d) contacting the cell with an indicator solution for determining whether the test compound is cytotoxic to the cell.

In another aspect, the present invention includes a reporter assay for identifying a compound that modulates that activity of a gene of interest. The reporter assay, comprises the steps of: (a) providing an expression system, the expression system comprising (i) a cell and (ii) a construct comprising a promoter region associated with said gene of interest operably linked to an enzyme associated with HCV RNA replication; (b) contacting the expression system with a test compound; and (c) contacting the expression system with a compound capable of detecting expression of the enzyme associated with HCV RNA replication. The enzyme associated with HCV RNA replication is desirably NS3 protease, and the compound capable of detecting expression of the enzyme associated with HCV RNA replication is desirably a FRET peptide.

In another aspect, the present invention includes a cell having ATCC Accession No. PTA-4583.

BRIEF DESCRIPTION OF THE DRAWINGS

FIG. 2 shows the nucleic acid sequence of the HCV Replicon used in an assay of the present invention.

FIG. 3 shows the amino acid sequence of the HCV Replicon used in an assay of the present invention.

FIG. 4 shows the 96-well layout used in an assay of the present invention.

FIG. 7A shows the enzyme activity in each well after contact with test compounds.

FIG. 7B shows the cytotoxicity activity in each well after contact with test compounds.

DETAILED DESCRIPTION OF THE INVENTION

Figure 1:
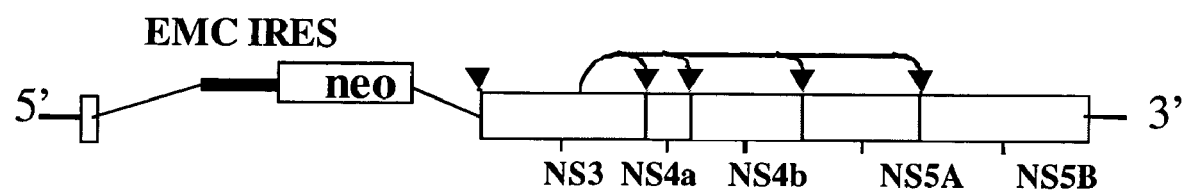
FIG. 1 shows the molecular construct of the HCV Replicon used in an assay of the present invention.

The present invention includes a cell-based HCV assay for measuring the ability of compounds to inhibit HCV RNA replication. An assay of the present invention desirably include a first cytotoxicity assay step which measures the conversion of an indicator solution to a fluorescent product, to determine if a test compound is cytotoxic to a cell; and a second inhibition assay step, to determine if the test compound inhibits HCV RNA replication. Desirably, an assay of the present invention includes the use of cells transfected with a HCV replicon.

The ability of the HCV replicon to replicate is highly dependent on the amounts or activity of host cell factors. Therefore, any slight toxicity may have significant effects on viral protein expression and ultimately on any assay which examines the effect of compounds on HCV replication. As such, the use of an indicator to assess cytotoxicity in an HCV replicon cell line in an assay of the present invention provides a significant advantage in the ability to address the issue of whether HCV inhibition is due to a specific compound-virus interaction or due to a subtle but toxic effect on the cellular replication machinery.

Accordingly, the present invention includes a dual assay useful for HTS that quantifies both the amount of HCV RNA replication inhibitory activity associated with a test compound, and the amount of cytotoxicity associated with that test compound. The dual assay is desirably conducted in a single well. Assays of the present invention permit for the mass screening of compounds specifically directed towards HCV replication, and permit viral RNA as well as viral proteins to be produced at levels consistently detectable using standard immunological and molecular biology methods. These consistent levels are amendable for HTS of compounds specific for the HCV replicon since effects either toxic to the cell or specific to the replicon can be differentiated and quantitated.

In an assay of the present invention, a first cytotoxicity assay step measures the conversion of an Alamar Blue solution to a fluorescent product while a second inhibition assay step that uses a fluorescence resonance energy transfer (FRET) protease substrate specifically measures the amount of HCV NS3 protease activity present and relates that activity to HCV RNA amounts. The first cytotoxicity assay step permits the determination of selectivity of the test compound under consideration for the cells in the assay. The use of Alamar Blue solution permits the assay steps to be run in the same well, as the Alamar Blue solution is non-lethal to the cells. An assay of the present invention has been validated and compared with quantitative reverse-transcriptase polymerase chain reaction (qRT-PCR) and western blot analysis using interferon-$\alpha$, a known HCV inhibitor. An assay of the present invention yielded fifty-percent effective concentration (EC50) values of 1.9, 2.9 and 5.3 units for the western, FRET and qRT-PCR assays, respectively. Assays of the present invention are amenable for HTS to identify compounds which inhibit HCV RNA replication, providing a convenient and economical assay comparable to qRT-PCR.

HCV is a plus (+) strand RNA virus which is well characterized, having a length of approximately 9.6 kb and a single, long open reading frame (ORF) encoding an approximately 3000-amino acid polyprotein (Lohman et al., *Science* 285:110–113 (1999), expressly incorporated by reference in its entirety). The ORF is flanked at the 5' end by a nontranslated region that functions as an internal ribosome entry site (IRES) and at the 3' end by a highly conserved sequence essential for genome replication (Lohman, supra). The structural proteins are in the $NH_2$-terminal region of the polyprotein and the nonstructural proteins (NS) 2 to 5B in the remainder.

In an assay of the present invention, a HCV replicon was used in a cell culture system and was made as set forth below in Materials and Methods. The HCV replicon was based on a full-length consensus genome cloned from viral RNA isolated from an infected human liver. As shown in the molecular construct set forth in FIG. 1, a HCV replicon useful in an assay of the present invention includes a neomycin (neo) selectable marker protein translated from the native HCV internal ribosome entry site (IRES) element and non-structural proteins translated by the IRES from encephalomyocarditis virus (Lohman, supra). The known viral specific enzymatic activities provided by the replicon include the protease (NS3) and activator of the protease (NS4A), helicase (NS3), ATPase (NS3) and RNA dependent RNA polymersase (NS5B). Expression of neo is solely dependent on active HCV RNA replication in cells, and the viral gene products NS3 to NS5B are believed to be essential for HCV RNA replication and are the primary targets for inhibitor identification. For purposes of the present invention, viral gene products which are "associated" with HCV RNA replication include any and all viral gene products believed to be essential for HCV RNA replication.

Methods used to quantitate HCV can be applied to the replicon and include quantitative RT-PCR (qRT-PCR) for RNA levels and immunological methods for proteins such as ELISA (Rodriguez-Lopez et. al., *J. Gen. Virol.* 80:727–738 (1999), expressly incorporated by reference in its entirety) or Western analysis (Pietschmann et al., *J. Virol.* 75:1253–1264 (2001), expressly incorporated by reference in its entirety).

An assay of the present invention consists of two parts. The first part is a cytotoxicity assay step which quantitates the amount of cytotoxicity associated with a test compound, as determined by the conversion of Alamar Blue dye. The second part is an inhibition assay step which quantitates the amount of NS3 protease activity associated with the test compound. Both measurements are then compared relative to control wells. This method provides a measure of cytotoxicity for each well and an indirect measure of HCV RNA levels. Inhibition of HCV RNA replication is expected to reduce the amount of viral proteins present, including NS3 protease. As such, inhibitory activity of test compounds on HCV RNA replication is indirectly measured by quantitating NS3 protease levels using a FRET assay. The results obtained with the FRET assay have been shown to be comparable to those obtained from qRT-PCR.

The following section sets forth materials and methods used in the present invention, and which were utilized in the Example set forth hereinbelow.

Materials and Methods

1. HCV Replicon Cell Line Preparation

The HCV replicon cell line was isolated from colonies as described by Lohman et al. al. (Lohman, supra) and used for all experiments. The HCV replicon has the nucleic acid sequence set forth in FIG. 2 (EMBL Accession No.: AJ242652; SEQ ID NO:1), the coding sequence of which is from 1801 nt–7758 nt. The coding sequence encodes the polypeptide having the sequence set forth in FIG. 3 (SEQ ID NO:2).

The cell line used in the present invention has been deposited as ATCC Accession No. PTA-4583 in the American Type Culture Collection, 10801 University Boulevard, Manassas, Va. 20110-2209 U.S.A. under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted.

The coding sequence of the published HCV replicon was synthesized by Operon Technologies, Inc. (Alameda, Calif.), and the full-length replicon was then assembled in plasmid pGem9zf(+) (Promega) using standard molecular biology techniques. The replicon consists of (i) the HCV 5' UTR fused to the first 12 amino acids of the capsid protein, (ii) the neomycin phosphotransferase gene (neo), (iii) the IRES from encephalomyocarditis virus (EMCV), and (iv) HCV NS3 to NS5B genes and the HCV3' UTR. Plasmid DNAs were linearized with ScaI and RNA transcripts were synthesized in vitro using the T7 MegaScript transcription kit (Ambion) according to manufacturer's directions.

To generate cell lines, $4 \times 10^6$ Huh-7 cells (kindly provided by R. Bartenschlager and available from Health Science Research Resources Bank, Japan Health Sciences Foundation) were electroporated (GenePulser System, Bio-Rad) with 10 ug of RNA transcript and plated into 100-mm dishes. After 24 h, selective media containing 1.0 mg/ml G418 was added and media was changed every 3 to 5 days. Approximately 4 weeks after electroporation, small colonies were visible which were isolated and expanded for further analysis. These cell lines were maintained at 37° C., 5% $CO_2$, 100% relative humidity in DMEM (Life Technologies #11965-084) with 10% heat inactivated calf serum (Sigma #F-2442), 100 U/ml of penicillin/streptomycin (Life Technologies #15140-122), Geneticin at 1 mg/ml (Life Technologies #10131-027). One of the cell lines which had approximately 3,000 copies of HCV replicon RNA/cell was used for development of the assay.

Other HCV replicons, as well as different genotypes, are suitable for use in assays of the present invention, and it is to be understood that assays of the present invention are not limited to any particular HCV replicon or cell line created therefrom. For example, in addition to the HCV replicon described above, HCV replicons suitable for use in assays of the present invention include, but are not limited to, those available from Apath, LLC. Also, it is understood that modifications of such HCV replicons may be made such that the replicon is useful in assays of the present invention.

2. RNA Detection

HCV RNA detection was conducted using RT-PCR, according to the manufacturer's instructions, using a Gibco-BRL Platinum Quantitative RT-PCR Thermoscript One-Step Kit on a Perkin-Elmer ABI Prism Model 7700 sequence detector. The primers for TaqMan were selected for use following analysis of RNA sequences with Primer Express Software from ABI. Primers used for detection of the plus strand RNA were 131F-5' GGGAGAGCCATAGTG-GTCTGC 3' (SEQ ID NO:3) and 231R-5' CCCAAATCTC-CAGGCATTGA 3' (SEQ ID NO:4) which amplify the HCV 5'UTR from nucleotides 131 to 231. The probe used for detection, 5' FAM-CGGAATTGCCAGGACGACCGG-BHQ1 3' (SEQ ID NO:5) was obtained from Biosearch Technologies. RNA's were purified from 96-wells using the RNAeasy 96 kit from Qiagen.

3. Western Analysis

Experiments were done in duplicate. Western analysis was performed according to the instructions for Amershams Chemiluminescence Immunology Kit (NEL105 Renaissance) using a Molecular Dynamics Storm 860 phosphoimager and associated software. The primary and secondary antibody dilutions were at 1 to 5,000. Antisera was generated by immunizing rabbits with purified NS3 protease made from an *E. Coli* expression vector encoding the first 181 amino acids of HCV 1a NS3 with subsequent boosts.

Bleeds were tested weekly and boosts continued until a positive signal on a control western was seen. Secondary antibody was a BioRad (#170–6515) Goat anti-Rabbit IgG HRP Conjugate. The protein samples for western analysis were from the same wells used for the FRET assay and were prepared by the addition of an equal volume of 2×SDS-PAGE buffer to the FRET assay mixture, heating and loading on a 10% gel for SDS-PAGE. Interferon alpha (IFN-α) was obtained from Sigma (#I-4276) and stored as recommended.

4. FRET Assay Preparation

To perform the HCV FRET screening assay, 96-well cell culture plates were used. The FRET peptide (Anaspec, Inc.) (Taliani et al. *Anal. Biochem.* 240:60–67 (1996), expressly incorporated by reference in its entirety) contains a fluorescence donor, EDANS, near one end of the peptide and an acceptor, DABCYL, near the other end. The fluorescence of the peptide is quenched by intramolecular resonance energy transfer (RET) between the donor and the acceptor, but as the NS3 protease cleaves the peptide the products are released from RET quenching and the fluorescence of the donor becomes apparent.

The assay reagent was made as follows: 5× cell Luciferase cell culture lysis reagent from Promega (#E153A) diluted to 1× with dH$_2$O, NaCl added to 150 mM final, the FRET peptide diluted to 20 uM final from a 2 mM stock. Cells were trypsinized, placed into each well of a 96-well plate and allowed to attach overnight. The next day, the test compounds were added to columns 1 through 10; column 11 was media only, and column 12 contained a titration of interferon as a control (1000 units for A12, B12, 100 units for C12, D12, 10 units for E12, F12 and 1 unit for G12, H12). In addition, replicon cells in A12, B12 can be replaced, if desired, with naïve Huh-7 cells as a negative background control. The plates were then placed back in the incubator. FIG. 4 shows the layout for HTS of the replicon cell line in a 96-well plate. In FIG. 4, labels are as followed: "Screen" denotes wells with test compound; "1-HCV" denotes control replicon wells (100% activity), "Inhibited" denotes wells containing the highest amount of control inhibitor (100% inhibition), and was used to determine background for each plate; "Titration" denotes the titration of interferon, and was used as a sensitivity control. Units of interferon from the top of row 12 in duplicate are 1000, 100, 10, and 1.

5. FRET Assay and Cytotoxicity Assay Steps

Subsequent to addition of the test compounds described above (FRET Assay Preparation), at various times the plate was removed and Alamar Blue solution (Trek Diagnostics, #00–100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold.

Compound analysis was determined by quantification of the relative HCV replicon inhibition and the relative cytotoxicity values. To calculate cytotoxicity values, the average Alamar Blue fluorescence signals from the control wells in row 11 (FIG. 4) were set as 100% non-toxic. The individual signals in each of the compound test wells were then divided by the average control signal and multiplied by 100% to determine percent cytotoxicity. To calculate the HCV replicon inhibition values, an average background value FRET signal was obtained from the two wells containing the highest amount of interferon at the end of the assay period. These numbers were similar to those obtained from naïve Huh-7 cells.

The background numbers were then subtracted from the average FRET signal obtained from the control wells in row 11 (FIG. 4) and this number was used as 100% activity. The individual signals in each of the compound test wells were then divided by the averaged control values after background subtraction and multiplied by 100% to determine percent activity. EC$_{50}$ values for an interferon titration were calculated as the concentration which caused a 50% reduction in HCV RNA, HCV protein amounts or FRET activity. The two numbers generated for the compound plate, percent cytotoxicity and percent activity were used to determine compounds of interest for further analysis.

6. Calculation of Assay Variation

The following formula was used to calculate the variation in the FRET assay. Z' is a measure of the distance between the standard deviations for the signal versus the noise of the assay:

$$Z'=1-((3*asds+3*asdb)/(as-ab))$$

Asds=standard deviation of the signal
Asdb=standard deviation of the background
As=average signal
Ab=average background signal
(Zhang et al., *J. Biomolecular Screening* (4) 2:67–73 (1999), expressly incorporated by reference in its entirety).

EXAMPLE

An assay of the present invention was prepared and conducted in the manner set forth above in Materials and Methods. The HTS assay was designed to indirectly measure RNA levels through the use of a specific NS3 protease fluorescence substrate which yields a fluorescent signal upon cleavage. To ensure that the NS3 protease substrate could only be cleaved by the NS3 protease and not by any cellular proteases present in the replicon cell lysates, the substrate was added to individual wells containing crude lysates made from either naive Huh-7 cells, HepG-2 cells or HeLa cells. The substrate was found to only yield a substantial increase in fluorescence in cells containing either the HCV replicon or in cells expressing the NS3 enzyme, indicating that the assay was specific for HCV protease.

Prior to the FRET assay step, a solution of Alamar Blue was added to the same plates in a cytotoxicity assay step, allowing direct quantification of the level of toxicity in that well. Only compounds which show no apparent toxicity but significantly decrease the amount of NS3 protease activity were further analyzed for HCV inhibitory activity.

In order to validate the FRET assay for HTS, the relationship between viral RNA levels and the amount of NS3 activity present was quantitated. One consideration of using the NS3 protease as a general indicator of RNA levels is that the $t_{1/2}$ life of the RNA compared to the protein may be substantially different (Lohman, supra). This could result in a substantial drop in RNA levels rather quickly compared to protein amounts. To compensate for this difference, the cells were exposed to interferon alpha (IFN-α), a known HCV inhibitor (Lauer G. M. and B. D. Walker, *N. Engl. J. Med.* 345(1):41–52 (2001); Blight et al., *Science,* 290:1972–1974 (2000); Collier J. and R. Chapman, *BioDrugs,* 15(4):225–238 (2001), each of which is expressly incorporated by reference in its entirety), for a period of days, allowing the cells to magnify the effect and let the amount of NS3 present decrease relative to controls.

The validation of the assay was accomplished by the use of quantitative RT-PCR (qRT-PCR) for viral RNA levels, quantification of the amount of NS3 present by scanning of a Western blot for protein levels and measurement of NS3 protease activity using the FRET assay. The samples for these measurements were from 2 plates prepared the same day and treated at the same time with a titration of IFN-α. One plate was used for preparation of RNA for quantitative RT-PCR while the other plate was used for FRET. Samples from the same wells after the FRET assay were used for Western analysis. Compound plates were then used to ensure that the procedure was applicable under conditions of HTS.

Figure 5:
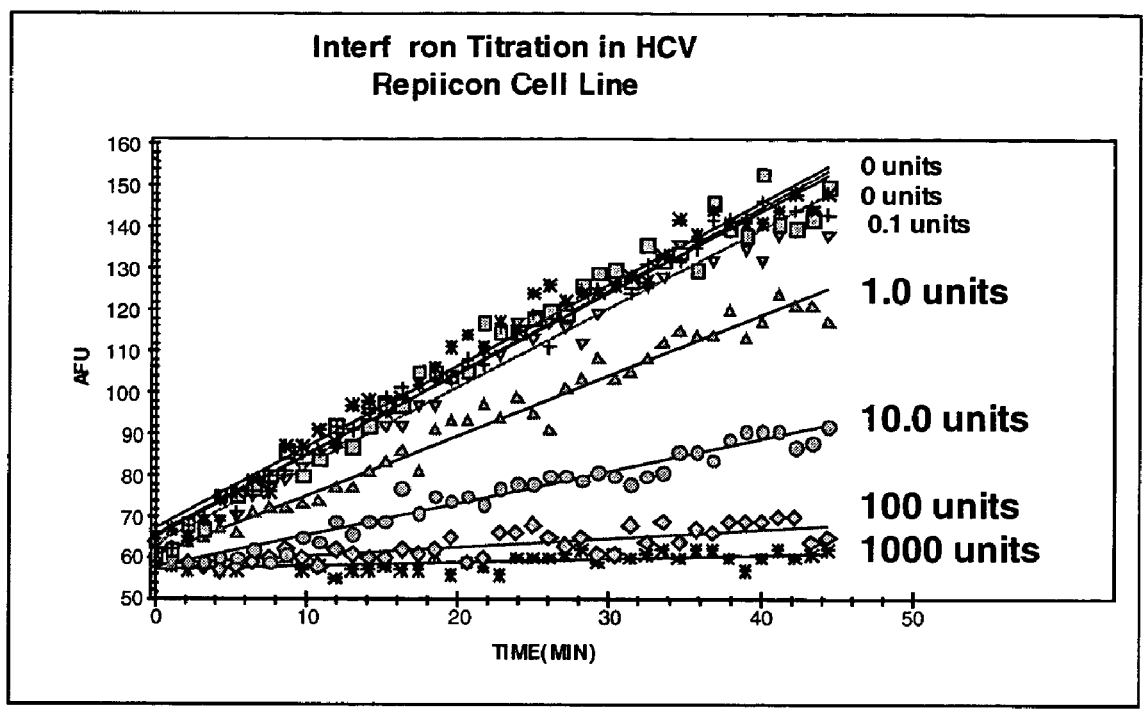
FIG. 5 shows the results of Interferon Titration in the HCV Replicon cell line used in an assay of the present invention.

The results of a FRET assay with IFN-α titration following 96 hours of incubation are shown in FIG. 5 as a continuous kinetic graph. FIG. 5 shows the measurement of the increase in fluorescence of the HCV FRET peptide in the HCV cell line and the effect of exposure to various interferon concentrations. The units per ml of IFN-α used for the different wells are listed to the right of the pertinent graphs. The assay is linear over a period of 40 minutes. As seen in FIG. 5, in the absence of IFN-α, the FRET signal is increased with time and is linear for at least 30 minutes. A decrease in the rate of FRET activity is clearly evident in the graph with increasing IFN-α concentration. The titration was from 0.1 units to 1,000 units per milliliter with control wells containing IFN-α dilution buffer only.

Figure 6A:
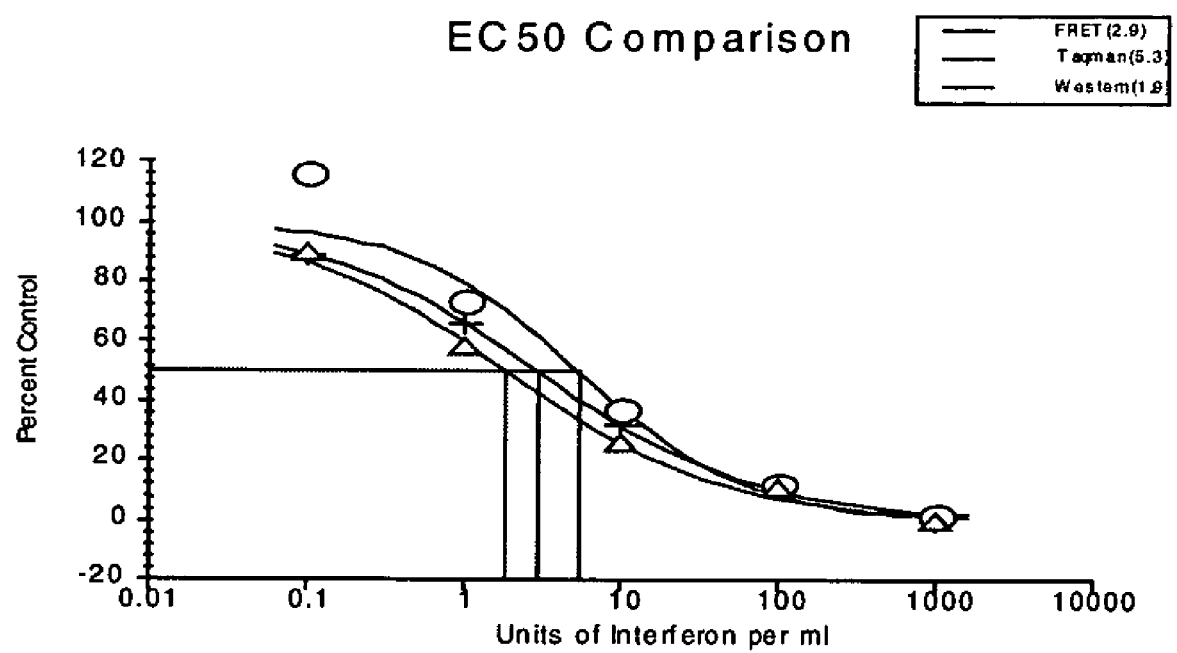
FIG. 6A shows an EC50 comparison of typical values determined by FRET, RT-PCR or Western analysis for titration of interferon in the HCV replicon cell line.
Figure 6B:
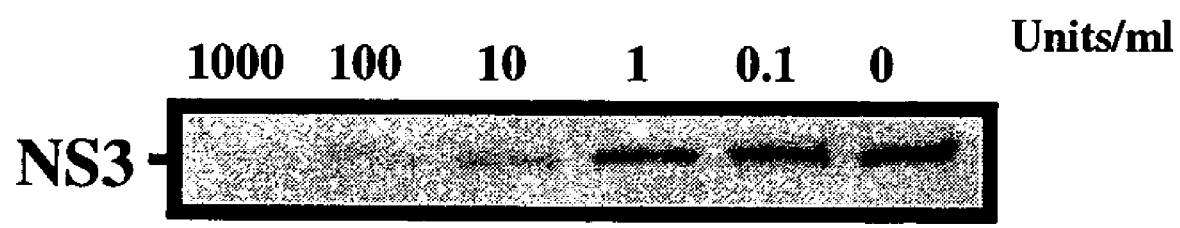
FIG. 6B shows a Western immunoblot using an anti-NS3 protease serum for the determination of $EC_{50}$ of IFN-$\alpha$.

Calculations involved subtracting the final background fluorescence signal while using the control wells as 100% activity. These numbers from the linear range are required for determination of the IFN-α $EC_{50}$. Similarly, RNA levels were measured by qRT-PCR while the amount of NS3 protein present in each well was quantitated by scanning a Western immunoblot. An $EC_{50}$ was determined for all three methods by normalizing to the controls for each measurement. FIG. 6A shows a comparison of typical values determined by FRET, RT-PCR or scanning of a western blot for titration of interferon in the HCV replicon cell line, and also shows values for quantification of NS3 protease specific bands (FIG. 6B) by phosphorimaging. Each value in FIG. 6A represents a well of a 96-well plate at a single interferon concentration relative to a control value. Data at the lowest concentration of interferon tended to contain more variation. FIG. 6B shows the Western immunoblot using an anti-NS3 protease serum for the determination of $EC_{50}$ of IFN-α.

The results shown in FIG. 6A indicate $EC_{50}$ values (in units of IFN-α per milliliter) of 1.9 for the Western, 2.9 for the FRET and 5.3 for RT-PCR. These values are within 3-fold of one another and indicate equivalency between the assay methods. This demonstrates the utility of the FRET assay method for inhibitor titration in an assay of the present invention and provides a comparison of a HTS format to the conventional qRT-PCR method of HCV quantification.

A random compound plate was used in a method test of both the Alamar Blue assay and the FRET HCV replicon assay steps. The results are presented in FIGS. 7A and 7B for both the FRET and Alamar Blue assay as diagrammed in FIG. 4. FIG. 7A shows the percentage of activity in each well following FRET readings and performing the calculations described above for the endpoint reading from cycle 21 of the FRET assay. In FIG. 7A, lower numbers represent less activity present and indicate that the HCV replicon is inhibited. Wells F2 and G5 (underlined and enlarged) indicate that the compounds present in these wells inhibited the HCV replicon approximately 73% and 99% respectively.

FIG. 7B shows Alamar Blue readings from the random compound plate expressed as a measure of cytotoxicity. Wells corresponding to F2 and G5 (underlined and enlarged) indicate that compound present in F2 shows very little toxicity while compound in G5 has substantial toxicity. Comparing the results of the FRET assay with the Alamar assay it is likely that the inhibition of the HCV replicon for G5 is due to a toxic mechanism while the inhibition due to compound in F2 is not toxic in this assay, suggesting the compound may be specific for HCV.

In general, the majority of compounds did not cause a significant variation in either the FRET or Alamar Blue assay indicating acceptable results amenable to HTS. The FRET activity yielded a 12.7% standard deviation in wells containing control media (FIG. 7A, column 11). In the IFN-α control samples, a clear inhibition was observed, the $EC_{50}$ was close to or slightly lower than the lowest concentration of IFN-α used (FIG. 7A, column 11). The Alamar Blue measurements in this plate yielded a variation of 4% for the cytotoxicity measurements in wells containing control media (FIG. 7B, column 11). Approximately 18% cytotoxicity was observed in the wells with the highest concentration of IFN-α (1000 units, FIG. 7B, columns A12 and B12), but no apparent Alamar Blue staining change was seen at lower concentrations of IFN-α. In the compound test area, two compounds showed a noticeable reduction in FRET activity, down to 27% and 1% detectable activity, respectively, of the control level (FIG. 7A, columns F2 and G5).

Inspection of the numbers and comparison of FIGS. 7A and 7B indicate a toxic compound is present in well G5 due to the decrease in FRET activity along with a corresponding decrease for the Alamar assay. Well F2, however, was seen to have a noticeable decrease in FRET activity without a corresponding decrease in the Alamar Blue measurement, indicating HCV replicon inhibition without measurable toxicity for this compound. Therefore, this compound was chosen for further evaluation.

To confirm that the variation in the FRET assay would remain acceptable, 40 additional compound plates were used to quantitate the variation using a statistical analysis to measure the Z' statistic (Materials and Methods). The Z' statistic is a measure of the distance between the standard deviations for the signal versus the noise of the assay. This analysis was used since the signal to noise in the assay was usually only 3-fold which is less than the Alamar signal to noise of approximately 8-fold indicating less tolerance for variation in the assay. An assay is considered acceptable if the Z' statistic is 0.5 or greater indicating acceptable signal to noise scatter in the plates.

Figure 8:
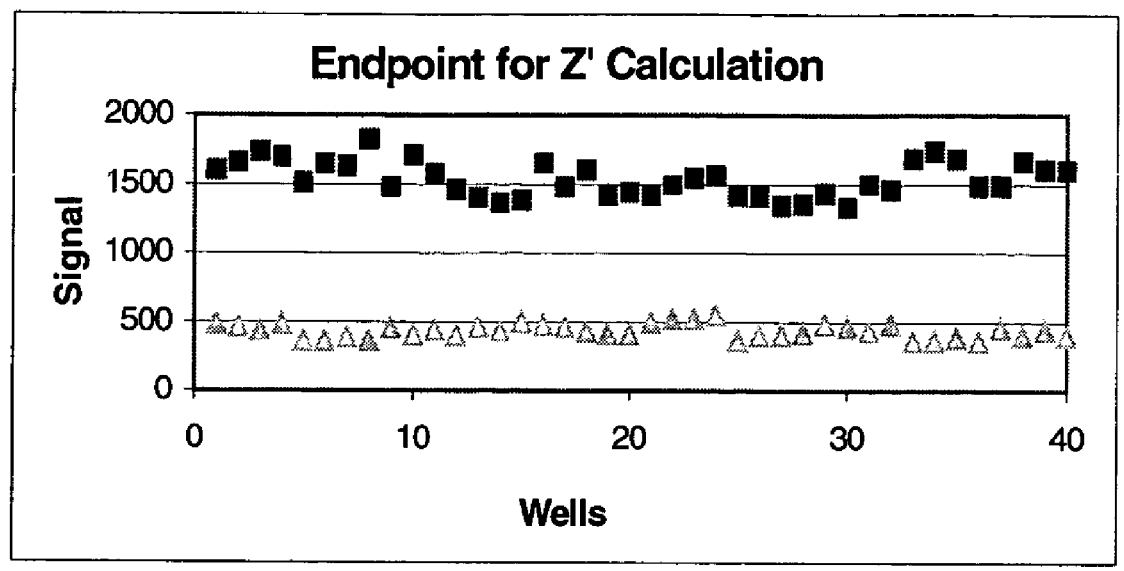
FIG. 8 shows a graphical representation of the variation within an assay of the present invention.

Forty plates were used to measure the standard deviations and the number distribution between the endpoint signal obtained for the controls and the signal obtained for the background. FIG. 8 shows a graphical representation of the averaged numbers from 40 separate compound plates used in the Z' calculation. The numbers at a signal of approximately 500 are the readings from the wells containing 1000 units of interferon and are considered to have 0% FRET activity. The numbers at a signal of approximately 1500 are from wells containing buffer only and are considered as 100% FRET activity. The Z' measurement calculates the distance as a fraction between the two number distributions in terms of the means of those distributions.

Using this calculation, a Z' of 0.62 was obtained indicating a plate to plate variation acceptable for HTS. In addition, this measurement can be used on individual plates to determine if the controls were acceptable validating the data for a particular plate.

Discussion

Assays of the present invention may be conducted in a 96-well format, as demonstrated by the dose response curve generated by IFN-α and yields results comparable to qRT-PCR, and are amenable to an even greater degree of miniaturization, such as a 384 or smaller based cell culture assay.

As illustrated in FIGS. 7A and 7B, assays of the present invention are capable of measuring toxicity associated with a test compound as well as inhibitory activity associated with the test compound in the same well, thereby providing a method to prioritize compounds according to their inhibitory profile versus HCV as well as according to their toxicity profile. The variation associated with such assays is also statistically acceptable, as illustrated in FIG. 8. The cytotoxicity assay reagents, such as Alamar Blue, are desirably easily removed and are not deleterious to the cells.

Assays of the present invention have distinct advantages when compared to qRT-PCR or other methods in that assays of the present invention may take place in-situ in a detergent based crude cell lysate, which requires no further preparation prior to performing the assays. Assays of the present invention do not involve numerous manipulations to add or subtract reagents after addition of test compounds, and are desirably based on a viral protein which is required by the HCV replicon for replication. The FRET protease substrate peptide, which is resistant to cleavage by endogenous Huh-7 cellular proteases over the assay time period, is efficiently recognized by the replicon-based NS3 enzyme. Given that the original purpose of the substrate was to monitor the in-vitro cleavage (Taliani, supra) of this substrate by purified rather than crude enzyme, it is probable that the substrate can still be cleaved by the many different genotypes of HCV NS3, thereby providing greater utility.

The present invention also includes reporter assays. Reporter assays of the present invention include the use of a HCV protease and FRET peptide combination. The FRET substrate is relatively resistant to Huh-7, HeLa and HepG2 cellular proteases, indicating that it is very specific for HCV protease and therefore likely resistant to cellular proteases in other cell types. Placement of the HCV NS3 protease in a mammalian or bacterial expression system, or in the context of other viruses, allows the FRET assay to provide a sensitive method to use the viral protein in a wider cell repertoire. Such a reporter system is useful in a similar manner to known luciferase/beta-galactosidase systems, and are useful for the measurement of protein production, promoter strength, cell viability or other combinations. Adaptation of this method of assay is also possible with other viral proteases, provided a suitable and specific assay substrate is synthesized. The present invention also includes a cell line having ATCC Accession No. PTA-4583.

While the invention has been described in connection with specific embodiments therefore, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims. All references cited herein are expressly incorporated in their entirety.

What is claimed is:

1. A cell-based assay for identifying a compound that inhibits HCV RNA replication, comprising performing, in a single well, the steps of:

(a) providing cells containing an HCV replicon which expresses an HCV NS3 protease,
   (b) contacting said cells with a test compound,
   (c) contacting said cells with an indicator of cytotoxicity and measuring cytotoxicity, and
   (d) contacting said cells with a FRET peptide NS3 protease substrate and measuring fluorescence;

wherein a decrease of NS3 protease activity, indicated by inhibiting an increase in FRET fluorescence, identifies the test compound as inhibiting HCV RNA replication.

2. The cell-based assay of claim 1, wherein said HCV replicon comprises a polynucleotide having the nucleic acid sequence set forth in SEQ ID NO: 1.

3. The cell-based assay of claim 1, wherein said HCV replicon encodes a polypeptide having the amino acid sequence set forth in SEQ ID NO:2.

4. The cell-based assay of claim 1, wherein said HCV replicon comprises the molecular construct set forth in FIG. 1.

5. The cell-based assay of claim 1, wherein said cells are cells having ATCC Accession No. PTA-4583.

6. The cell-based assay of claim 1, wherein the indicator of cytotoxicity is an Alamar Blue solution.

7. The cell-based assay of claim 1, wherein said cell-based assay is performed in a high-throughput manner.

8. A cell-based assay for identifying a compound that inhibits HCV RNA replication, comprising performing, in a single well, the steps of:
   (a) providing cells having ATCC Accession No. PTA-4583, containing an HCV replicon which expresses an HCV NS3 protease,
   (b) contacting said cells with a test compound,
   (c) contacting said cells with an indicator of cytotoxicity and measuring cytotoxicity, and
   (d) contacting said cells with a FRET peptide NS3 protease substrate and measuring fluorescence;
wherein a decrease of NS3 protease activity, indicated by inhibiting an increase in FRET fluorescence, identifies the test compound as inhibiting HCV RNA replication.

* * * * *

SEQUENCE LISTING

```
<160> NUMBER OF SEQ ID NOS: 5

<210> SEQ ID NO 1
<211> LENGTH: 7989
<212> TYPE: DNA
<213> ORGANISM: Artificial
<220> FEATURE:
<223> OTHER INFORMATION: HCV Replicon

<400> SEQUENCE: 1
gccagccccc gattgggggc gacactccac catagatcac tcccctgtga ggaactactg      60
tcttcacgca gaaagcgtct agccatggcg ttagtatgag tgtcgtgcag cctccaggac     120
cccccctccc gggagagcca tagtggtctg cggaaccggt gagtacaccg gaattgccag     180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaaggg cgcgccatga ttgaacaaga tggattgcac gcaggttctc     420
```

-continued

```
cggccgcttg ggtggagagg ctattcggct atgactgggc acaacagaca atcggctgct      480
ctgatgccgc cgtgttccgg ctgtcagcgc aggggcgccc ggttcttttt gtcaagaccg      540
acctgtccgg tgccctgaat gaactgcagg acgaggcagc gcggctatcg tggctggcca      600
cgacgggcgt tccttgcgca gctgtgctcg acgttgtcac tgaagcggga agggactggc      660
tgctattggg cgaagtgccg gggcaggatc tcctgtcatc tcaccttgct cctgccgaga      720
aagtatccat catggctgat gcaatgcggc ggctgcatac gcttgatccg gctacctgcc      780
cattcgacca ccaagcgaaa catcgcatcg agcgagcacg tactcggatg aagccggtc       840
ttgtcgatca ggatgatctg gacgaagagc atcagggct cgcgccagcc gaactgttcg       900
ccaggctcaa ggcgcgcatg cccgacgcg aggatctcgt cgtgacccat ggcgatgcct       960
gcttgccgaa tatcatggtg gaaaatggcc gcttttctgg attcatcgac tgtggccggc    1020
tgggtgtggc ggaccgctat caggacatag cgttggctac ccgtgatatt gctgaagagc    1080
ttggcggcga atgggctgac cgcttcctcg tgctttacgg tatcgccgct cccgattcgc    1140
agcgcatcgc cttctatcgc cttcttgacg agttcttctg agtttaaaca gaccacaacg    1200
gtttccctct agcgggatca attccgcccc tctccctccc cccccctaa cgttactggc     1260
cgaagccgct tggaataagg ccggtgtgcg tttgtctata tgttattttc caccatattg    1320
ccgtcttttg gcaatgtgag ggcccggaaa cctggccctg tcttcttgac gagcattcct    1380
aggggtcttt cccctctcgc caaaggaatg caaggtctgt tgaatgtcgt gaaggaagca    1440
gttcctctgg aagcttcttg aagacaaaca acgtctgtag cgaccctttg caggcagcgg    1500
aaccccccac ctggcgacag gtgcctctgc ggccaaaagc cacgtgtata agatacacct    1560
gcaaaggcgg cacaacccca gtgccacgtt gtgagttgga tagttgtgga aagagtcaaa    1620
tggctctcct caagcgtatt caacaagggg ctgaaggatg cccagaaggt accccattgt    1680
atgggatctg atctggggcc tcggtgcaca tgctttacat gtgtttagtc gaggttaaaa    1740
aacgtctagg ccccccgaac cacggggacg tggttttcct ttgaaaaaca cgataatacc    1800
atggcgccta ttacggccta ctcccaacag acgcgaggcc tacttggctg catcatcact    1860
agcctcacag gccgggacag gaaccaggtc gaggggagg tccaagtggt ctccaccgca     1920
acacaatctt tcctgcgac ctgcgtcaat ggcgtgtgtt ggactgtcta tcatggtgcc     1980
ggctcaaaga cccttgccgg cccaaagggc ccaatcaccc aaatgtacac caatgtggac    2040
caggacctcg tcggctggca agcgcccccc ggggcgcgtt ccttgacacc atgcacctgc    2100
ggcagctcgg acctttactt ggtcacgagg catgccgatg tcattccggt gcgccggcgg    2160
ggcgacagca gggggagcct actctccccc aggcccgtct cctacttgaa gggctcttcg    2220
ggcggtccac tgctctgccc ctcggggcac gctgtgggca tctttcgggc tgccgtgtgc    2280
acccgagggg ttgcgaaggc ggtggacttt gtacccgtcg agtctatgga aaccactatg    2340
cggtccccgg tcttcacgga caactcgtcc cctccggccg taccgcagac attccaggtg    2400
gcccatctac acgcccctac tggtagcggc aagagcacta aggtgccggc tgcgtatgca    2460
gcccaagggt ataaggtgct tgtcctgaac ccgtccgtcg ccgccaccct aggtttcggg    2520
gcgtatatgt ctaaggcaca tggtatcgac cctaacatca gaaccggggt aaggaccatc    2580
accacgggtg cccccatcac gtactccacc tatggcaagt ttcttgccga cggtggttgc    2640
tctgggggcg cctatgacat cataatatgt gatgagtgcc actcaactga ctcgaccact    2700
atcctgggca tcggcacagt cctggaccaa gcggagacgg ctggagcgcg actcgtcgtg    2760
```

-continued

```
ctcgccaccg ctacgcctcc gggatcggtc accgtgccac atccaaacat cgaggaggtg    2820
gctctgtcca gcactggaga atccccttt tatggcaaag ccatcccat cgagaccatc     2880
aagggggga ggcacctcat tttctgccat tccaagaaga aatgtgatga gctcgccgcg     2940
aagctgtccg gcctcggact caatgctgta gcatattacc ggggccttga tgtatccgtc    3000
ataccaacta gcggagacgt cattgtcgta gcaacggacg ctctaatgac gggctttacc    3060
ggcgatttcg actcagtgat cgactgcaat acatgtgtca cccagacagt cgacttcagc    3120
ctggacccga ccttcaccat tgagacgacg accgtgccac aagacgcggt gtcacgctcg    3180
cagcggcgag gcaggactgg taggggcagg atgggcattt acaggtttgt gactccagga    3240
gaacggccct cgggcatgtt cgattcctcg gttctgtgcg agtgctatga cgcgggctgt    3300
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttcccctac    3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca gcgtggtcat tgtgggcagg    3780
atcatcttgt ccggaaagcc ggccatcatt cccgacaggg aagtcccttta ccgggagttc    3840
gatgagatgg aagagtgcgc ctcacacctc ccttacatcg aacagggaat gcagctcgcc    3900
gaacaattca acagaaggc aatcgggttg ctgcaaacag ccaccaagca agcggaggct    3960
gctgctcccg tggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct gggggatgg gtggccgccc aacttgctcc tcccagcgct    4200
gcttctgctt tcgtaggcgc cggcatcgct ggagcggctg ttggcagcat aggccttggg    4260
aaggtgcttg tggatattt ggcaggttat ggagcagggg tggcaggcgc gctcgtggcc    4320
tttaaggtca tgagcggcga gatgccctcc accgaggacc tggttaacct actccctgct    4380
atcctctccc ctggcgccct agtcgtcggg gtcgtgtgcg cagcgatact gcgtcggcac    4440
gtgggcccag ggaggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc cctgccgcg attgccggga    4740
gtccccttct tctcatgtca acgtgggtac aagggagtct ggcggggcga cggcatcatg    4800
caaaccacct gccatgtgg agcacagatc accggacatg tgaaaaacgg ttccatgagg    4860
atcgtggggc ctaggacctg tagtaacacg tggcatggaa cattccccat taacgcgtac    4920
accacgggcc cctgcacgcc ctcccggcg ccaaattatt ctaggcgct gtggcgggtg    4980
gctgctgagg agtacgtgga ggttacgcgg gtggggatt tccactacgt gacgggcatg    5040
accactgaca acgtaaagtg cccgtgtcag gttccggccc ccgaattctt cacagaagtg    5100
gatggggtgc ggttgcacag gtacgctcca gcgtgcaaac ccctcctacg ggaggaggtc    5160
```

```
acattcctgg tcgggctcaa tcaatacctg gttgggtcac agctcccatg cgagcccgaa    5220
ccggacgtag cagtgctcac ttccatgctc accgacccct cccacattac ggcggagacg    5280
gctaagcgta ggctggccag gggatctccc ccctccttgg ccagctcatc agctagccag    5340
ctgtctgcgc cttccttgaa ggcaacatgc actacccgtc atgactcccc ggacgctgac    5400
ctcatcgagg ccaacctcct gtggcggcag gagatgggcg ggaacatcac ccgcgtggag    5460
tcagaaaata aggtagtaat tttggactct ttcgagccgc tccaagcgga ggaggatgag    5520
agggaagtat ccgttccggc ggagatcctg cggaggtcca ggaaattccc tcgagcgatg    5580
cccatatggg cacgcccgga ttacaaccct ccactgttag agtcctggaa ggacccggac    5640
tacgtccctc cagtggtaca cgggtgtcca ttgccgcctg ccaaggcccc tccgatacca    5700
cctccacgga ggaagaggac ggttgtcctg tcagaatcta ccgtgtcttc tgccttggcg    5760
gagctcgcca caaagacctt cggcagctcc gaatcgtcgg ccgtcgacag cggcacggca    5820
acggcctctc ctgaccagcc ctccgacgac ggcgacgcgg gatccgacgt tgagtcgtac    5880
tcctccatgc cccccttga gggggagccg gggatcccg atctcagcga cgggtcttgg    5940
tctaccgtaa gcgaggaggc tagtgaggac gtcgtctgct gctcgatgtc ctacacatgg    6000
acaggcgccc tgatcacgcc atgcgctgcg gaggaaacca agctgcccat caatgcactg    6060
agcaactctt tgctccgtca ccacaacttg gtctatgcta caacatctcg cagcgcaagc    6120
ctgcggcaga agaaggtcac ctttgacaga ctgcaggtcc tggacgacca ctaccgggac    6180
gtgctcaagg agatgaaggc gaaggcgtcc acagttaagg ctaaacttct atccgtggag    6240
gaagcctgta agctgacgcc cccacattcg ccagatcta aatttggcta tggggcaaag    6300
gacgtccgga acctatccag caaggccgtt aaccacatcc gctccgtgtg gaaggacttg    6360
ctggaagaca ctgagacacc aattgacacc accatcatgg caaaaaatga ggttttctgc    6420
gtccaaccag agaagggggg ccgcaagcca gctcgcctta tcgtattccc agatttgggg    6480
gttcgtgtgt gcgagaaaat ggccctttac gatgtggtct ccaccctccc tcaggccgtg    6540
atgggctctt catacggatt ccaatactct cctggacagc gggtcgagtt cctggtgaat    6600
gcctggaaag cgaagaaatg ccctatgggc ttcgcatatg cacccgctg ttttgactca    6660 acggtcactg agaatgacat ccgtgttgag gagtcaatct accaatgttg tgacttggcc    6720
cccgaagcca gacaggccat aaggtcgctc acagagcggc tttacatcgg ggcccctg    6780 actaattcta aagggcagaa ctgccggcta tcgccggtgcc gcgcgagcgg tgtactgacg    6840
accagctgcg gtaatacccct cacatgttac ttgaaggccg ctgcggcctg tcgagctgcg    6900
aagctccagg actgcacgat gctcgtatgc ggagacgacc ttgtcgttat ctgtgaaagc    6960
gcggggaccc aagaggacga ggcgagccta cgggccttca cggaggctat gactagatac    7020 tctgccccc ctgggacccc gcccaaacca gaatacgact tggagttgat aacatcatgc    7080
tcctccaatg tgtcagtcgc gcacgatgca tctggcaaaa gggtgtacta tctcacccgt    7140
gaccccacca ccccccttgc gcgggctgcg tgggagacag ctagacacac tccagtcaat    7200
tcctggctag gcaacatcat catgtatgcg cccaccttgt gggcaaggat gatcctgatg    7260
actcatttct tctccatcct tctagctcag gaacaacttg aaaaagccct agattgtcag    7320
atctacgggg cctgttactc cattgagcca cttgacctac ctcagatcat tcaacgactc    7380
catggcctta gcgcattttc actccatagt tactctccag gtgagatcaa tagggtggct    7440
tcatgcctca ggaaacttgg ggtaccgccc ttgcgagtct ggagacatcg ggccagaagt    7500
```

-continued

```
gtccgcgcta ggctactgtc ccagggggggg agggctgcca cttgtggcaa gtacctcttc   7560
aactgggcag taaggaccaa gctcaaactc actccaatcc cggctgcgtc ccagttggat   7620
ttatccagct ggttcgttgc tggttacagc gggggagaca tatatcacag cctgtctcgt   7680
gcccgacccc gctggttcat gtggtgccta ctcctacttt ctgtagggt aggcatctat    7740 ctactcccca accgatgaac ggggagctaa acactccagg ccaataggcc atcctgtttt   7800
tttccttttt tttttttctt tttttttttt tttttttttt tttttttttt ttctcctttt   7860
tttttcctct ttttttcctt ttctttcctt tggtggctcc atcttagccc tagtcacggc   7920
tagctgtgaa aggtccgtga gccgcttgac tgcagagagt gctgatactg gcctctctgc   7980
agatcaagt                                                          7989
```

<210> SEQ ID NO 2
<211> LENGTH: 1985
<212> TYPE: PRT
<213> ORGANISM: Artificial
<220> FEATURE:
<223> OTHER INFORMATION: HCV Replicon

<400> SEQUENCE: 2

```
Met Ala Pro Ile Thr Ala Tyr Ser Gln Gln Thr Arg Gly Leu Leu Gly
1               5                   10                  15

Cys Ile Ile Thr Ser Leu Thr Gly Arg Asp Arg Asn Gln Val Glu Gly
            20                  25                  30

Glu Val Gln Val Val Ser Thr Ala Thr Gln Ser Phe Leu Ala Thr Cys
        35                  40                  45

Val Asn Gly Val Cys Trp Thr Val Tyr His Gly Ala Gly Ser Lys Thr
    50                  55                  60

Leu Ala Gly Pro Lys Gly Pro Ile Thr Gln Met Tyr Thr Asn Val Asp
65                  70                  75                  80

Gln Asp Leu Val Gly Trp Gln Ala Pro Pro Gly Ala Arg Ser Leu Thr
                85                  90                  95

Pro Cys Thr Cys Gly Ser Ser Asp Leu Tyr Leu Val Thr Arg His Ala
            100                 105                 110

Asp Val Ile Pro Val Arg Arg Arg Gly Asp Ser Arg Gly Ser Leu Leu
        115                 120                 125

Ser Pro Arg Pro Val Ser Tyr Leu Lys Gly Ser Ser Gly Gly Pro Leu
    130                 135                 140

Leu Cys Pro Ser Gly His Ala Val Gly Ile Phe Arg Ala Ala Val Cys
145                 150                 155                 160

Thr Arg Gly Val Ala Lys Ala Val Asp Phe Val Pro Val Glu Ser Met
                165                 170                 175

Glu Thr Thr Met Arg Ser Pro Val Phe Thr Asp Asn Ser Ser Pro Pro
            180                 185                 190

Ala Val Pro Gln Thr Phe Gln Val Ala His Leu His Ala Pro Thr Gly
        195                 200                 205

Ser Gly Lys Ser Thr Lys Val Pro Ala Ala Tyr Ala Ala Gln Gly Tyr
    210                 215                 220

Lys Val Leu Val Leu Asn Pro Ser Val Ala Ala Thr Leu Gly Phe Gly
225                 230                 235                 240

Ala Tyr Met Ser Lys Ala His Gly Ile Asp Pro Asn Ile Arg Thr Gly
                245                 250                 255

Val Arg Thr Ile Thr Thr Gly Ala Pro Ile Thr Tyr Ser Thr Tyr Gly
            260                 265                 270
```

-continued

```
Lys Phe Leu Ala Asp Gly Gly Cys Ser Gly Gly Ala Tyr Asp Ile Ile
            275                 280                 285
Ile Cys Asp Glu Cys His Ser Thr Asp Ser Thr Thr Ile Leu Gly Ile
        290                 295                 300
Gly Thr Val Leu Asp Gln Ala Glu Thr Ala Gly Ala Arg Leu Val Val
305                 310                 315                 320
Leu Ala Thr Ala Thr Pro Pro Gly Ser Val Thr Val Pro His Pro Asn
                325                 330                 335
Ile Glu Glu Val Ala Leu Ser Ser Thr Gly Glu Ile Pro Phe Tyr Gly
            340                 345                 350
Lys Ala Ile Pro Ile Glu Thr Ile Lys Gly Gly Arg His Leu Ile Phe
            355                 360                 365
Cys His Ser Lys Lys Lys Cys Asp Glu Leu Ala Ala Lys Leu Ser Gly
        370                 375                 380
Leu Gly Leu Asn Ala Val Ala Tyr Tyr Arg Gly Leu Asp Val Ser Val
385                 390                 395                 400
Ile Pro Thr Ser Gly Asp Val Ile Val Val Ala Thr Asp Ala Leu Met
                405                 410                 415
Thr Gly Phe Thr Gly Asp Phe Asp Ser Val Ile Asp Cys Asn Thr Cys
            420                 425                 430
Val Thr Gln Thr Val Asp Phe Ser Leu Asp Pro Thr Phe Thr Ile Glu
        435                 440                 445
Thr Thr Thr Val Pro Gln Asp Ala Val Ser Arg Ser Gln Arg Arg Gly
        450                 455                 460
Arg Thr Gly Arg Gly Arg Met Gly Ile Tyr Arg Phe Val Thr Pro Gly
465                 470                 475                 480
Glu Arg Pro Ser Gly Met Phe Asp Ser Ser Val Leu Cys Glu Cys Tyr
                485                 490                 495
Asp Ala Gly Cys Ala Trp Tyr Glu Leu Thr Pro Ala Glu Thr Ser Val
            500                 505                 510
Arg Leu Arg Ala Tyr Leu Asn Thr Pro Gly Leu Pro Val Cys Gln Asp
        515                 520                 525
His Leu Glu Phe Trp Glu Ser Val Phe Thr Gly Leu Thr His Ile Asp
        530                 535                 540
Ala His Phe Leu Ser Gln Thr Lys Gln Ala Gly Asp Asn Phe Pro Tyr
545                 550                 555                 560
Leu Val Ala Tyr Gln Ala Thr Val Cys Ala Arg Ala Gln Ala Pro Pro
                565                 570                 575
Pro Ser Trp Asp Gln Met Trp Lys Cys Leu Ile Arg Leu Lys Pro Thr
            580                 585                 590
Leu His Gly Pro Thr Pro Leu Leu Tyr Arg Leu Gly Ala Val Gln Asn
            595                 600                 605
Glu Val Thr Thr Thr His Pro Ile Thr Lys Tyr Ile Met Ala Cys Met
        610                 615                 620
Ser Ala Asp Leu Glu Val Val Thr Ser Thr Trp Val Leu Val Gly Gly
625                 630                 635                 640
Val Leu Ala Ala Leu Ala Ala Tyr Cys Leu Thr Thr Gly Ser Val Val
                645                 650                 655
Ile Val Gly Arg Ile Ile Leu Ser Gly Lys Pro Ala Ile Ile Pro Asp
            660                 665                 670
Arg Glu Val Leu Tyr Arg Glu Phe Asp Glu Met Glu Glu Cys Ala Ser
        675                 680                 685
His Leu Pro Tyr Ile Glu Gln Gly Met Gln Leu Ala Glu Gln Phe Lys
```

-continued

```
              690                 695                 700
Gln Lys Ala Ile Gly Leu Leu Gln Thr Ala Thr Lys Gln Ala Glu Ala
705                 710                 715                 720
Ala Ala Pro Val Val Glu Ser Lys Trp Arg Thr Leu Glu Ala Phe Trp
                725                 730                 735
Ala Lys His Met Trp Asn Phe Ile Ser Gly Ile Gln Tyr Leu Ala Gly
                740                 745                 750
Leu Ser Thr Leu Pro Gly Asn Pro Ala Ile Ala Ser Leu Met Ala Phe
                755                 760                 765
Thr Ala Ser Ile Thr Ser Pro Leu Thr Thr Gln His Thr Leu Leu Phe
770                 775                 780
Asn Ile Leu Gly Gly Trp Val Ala Ala Gln Leu Ala Pro Pro Ser Ala
785                 790                 795                 800
Ala Ser Ala Phe Val Gly Ala Gly Ile Ala Gly Ala Ala Val Gly Ser
                805                 810                 815
Ile Gly Leu Gly Lys Val Leu Val Asp Ile Leu Ala Gly Tyr Gly Ala
                820                 825                 830
Gly Val Ala Gly Ala Leu Val Ala Phe Lys Val Met Ser Gly Glu Met
                835                 840                 845
Pro Ser Thr Glu Asp Leu Val Asn Leu Leu Pro Ala Ile Leu Ser Pro
850                 855                 860
Gly Ala Leu Val Val Gly Val Val Cys Ala Ala Ile Leu Arg Arg His
865                 870                 875                 880
Val Gly Pro Gly Glu Gly Ala Val Gln Trp Met Asn Arg Leu Ile Ala
                885                 890                 895
Phe Ala Ser Arg Gly Asn His Val Ser Pro Thr His Tyr Val Pro Glu
                900                 905                 910
Ser Asp Ala Ala Ala Arg Val Thr Gln Ile Leu Ser Ser Leu Thr Ile
                915                 920                 925
Thr Gln Leu Leu Lys Arg Leu His Gln Trp Ile Asn Glu Asp Cys Ser
                930                 935                 940
Thr Pro Cys Ser Gly Ser Trp Leu Arg Asp Val Trp Asp Trp Ile Cys
945                 950                 955                 960
Thr Val Leu Thr Asp Phe Lys Thr Trp Leu Gln Ser Lys Leu Leu Pro
                965                 970                 975
Arg Leu Pro Gly Val Pro Phe Phe Ser Cys Gln Arg Gly Tyr Lys Gly
                980                 985                 990
Val Trp Arg Gly Asp Gly Ile Met  Gln Thr Thr Cys Pro  Cys Gly Ala
                995                 1000                1005
Gln Ile  Thr Gly His Val Lys  Asn Gly Ser Met Arg  Ile Val Gly
1010                1015                1020
Pro Arg  Thr Cys Ser Asn Thr  Trp His Gly Thr Phe  Pro Ile Asn
1025                1030                1035
Ala Tyr  Thr Thr Gly Pro Cys  Thr Pro Ser Pro Ala  Pro Asn Tyr
1040                1045                1050
Ser Arg  Ala Leu Trp Arg Val  Ala Ala Glu Glu Tyr  Val Glu Val
1055                1060                1065
Thr Arg  Val Gly Asp Phe His  Tyr Val Thr Gly Met  Thr Thr Asp
1070                1075                1080
Asn Val  Lys Cys Pro Cys Gln  Val Pro Ala Pro Glu  Phe Phe Thr
1085                1090                1095
Glu Val  Asp Gly Val Arg Leu  His Arg Tyr Ala Pro  Ala Cys Lys
1100                1105                1110
```

```
Pro Leu Leu Arg Glu Glu Val Thr Phe Leu Val Gly Leu Asn Gln
    1115                1120                1125

Tyr Leu Val Gly Ser Gln Leu Pro Cys Glu Pro Glu Pro Asp Val
    1130                1135                1140

Ala Val Leu Thr Ser Met Leu Thr Asp Pro Ser His Ile Thr Ala
    1145                1150                1155

Glu Thr Ala Lys Arg Arg Leu Ala Arg Gly Ser Pro Pro Ser Leu
    1160                1165                1170

Ala Ser Ser Ser Ala Ser Gln Leu Ser Ala Pro Ser Leu Lys Ala
    1175                1180                1185

Thr Cys Thr Thr Arg His Asp Ser Pro Asp Ala Asp Leu Ile Glu
    1190                1195                1200

Ala Asn Leu Leu Trp Arg Gln Glu Met Gly Gly Asn Ile Thr Arg
    1205                1210                1215

Val Glu Ser Glu Asn Lys Val Val Ile Leu Asp Ser Phe Glu Pro
    1220                1225                1230

Leu Gln Ala Glu Glu Asp Glu Arg Glu Val Ser Val Pro Ala Glu
    1235                1240                1245

Ile Leu Arg Arg Ser Arg Lys Phe Pro Arg Ala Met Pro Ile Trp
    1250                1255                1260

Ala Arg Pro Asp Tyr Asn Pro Pro Leu Leu Glu Ser Trp Lys Asp
    1265                1270                1275

Pro Asp Tyr Val Pro Pro Val His Gly Cys Pro Leu Pro Pro
    1280                1285                1290

Ala Lys Ala Pro Pro Ile Pro Pro Pro Arg Arg Lys Arg Thr Val
    1295                1300                1305

Val Leu Ser Glu Ser Thr Val Ser Ser Ala Leu Ala Glu Leu Ala
    1310                1315                1320

Thr Lys Thr Phe Gly Ser Ser Glu Ser Ser Ala Val Asp Ser Gly
    1325                1330                1335

Thr Ala Thr Ala Ser Pro Asp Gln Pro Ser Asp Asp Gly Asp Ala
    1340                1345                1350

Gly Ser Asp Val Glu Ser Tyr Ser Ser Met Pro Pro Leu Glu Gly
    1355                1360                1365

Glu Pro Gly Asp Pro Asp Leu Ser Asp Gly Ser Trp Ser Thr Val
    1370                1375                1380

Ser Glu Glu Ala Ser Glu Asp Val Val Cys Cys Ser Met Ser Tyr
    1385                1390                1395

Thr Trp Thr Gly Ala Leu Ile Thr Pro Cys Ala Ala Glu Glu Thr
    1400                1405                1410

Lys Leu Pro Ile Asn Ala Leu Ser Asn Ser Leu Leu Arg His His
    1415                1420                1425

Asn Leu Val Tyr Ala Thr Thr Ser Arg Ser Ala Ser Leu Arg Gln
    1430                1435                1440

Lys Lys Val Thr Phe Asp Arg Leu Gln Val Leu Asp Asp His Tyr
    1445                1450                1455

Arg Asp Val Leu Lys Glu Met Lys Ala Lys Ala Ser Thr Val Lys
    1460                1465                1470

Ala Lys Leu Leu Ser Val Glu Glu Ala Cys Lys Leu Thr Pro Pro
    1475                1480                1485

His Ser Ala Arg Ser Lys Phe Gly Tyr Gly Ala Lys Asp Val Arg
    1490                1495                1500
```

```
Asn Leu Ser Ser Lys Ala Val Asn His Ile Arg Ser Val Trp Lys
    1505                1510                1515

Asp Leu Leu Glu Asp Thr Glu Thr Pro Ile Asp Thr Thr Ile Met
    1520                1525                1530

Ala Lys Asn Glu Val Phe Cys Val Gln Pro Glu Lys Gly Gly Arg
    1535                1540                1545

Lys Pro Ala Arg Leu Ile Val Phe Pro Asp Leu Gly Val Arg Val
    1550                1555                1560

Cys Glu Lys Met Ala Leu Tyr Asp Val Val Ser Thr Leu Pro Gln
    1565                1570                1575

Ala Val Met Gly Ser Ser Tyr Gly Phe Gln Tyr Ser Pro Gly Gln
    1580                1585                1590

Arg Val Glu Phe Leu Val Asn Ala Trp Lys Ala Lys Lys Cys Pro
    1595                1600                1605

Met Gly Phe Ala Tyr Asp Thr Arg Cys Phe Asp Ser Thr Val Thr
    1610                1615                1620

Glu Asn Asp Ile Arg Val Glu Glu Ser Ile Tyr Gln Cys Cys Asp
    1625                1630                1635

Leu Ala Pro Glu Ala Arg Gln Ala Ile Arg Ser Leu Thr Glu Arg
    1640                1645                1650

Leu Tyr Ile Gly Gly Pro Leu Thr Asn Ser Lys Gly Gln Asn Cys
    1655                1660                1665

Gly Tyr Arg Arg Cys Arg Ala Ser Gly Val Leu Thr Thr Ser Cys
    1670                1675                1680

Gly Asn Thr Leu Thr Cys Tyr Leu Lys Ala Ala Ala Ala Cys Arg
    1685                1690                1695

Ala Ala Lys Leu Gln Asp Cys Thr Met Leu Val Cys Gly Asp Asp
    1700                1705                1710

Leu Val Val Ile Cys Glu Ser Ala Gly Thr Gln Glu Asp Glu Ala
    1715                1720                1725

Ser Leu Arg Ala Phe Thr Glu Ala Met Thr Arg Tyr Ser Ala Pro
    1730                1735                1740

Pro Gly Asp Pro Pro Lys Pro Glu Tyr Asp Leu Glu Leu Ile Thr
    1745                1750                1755

Ser Cys Ser Ser Asn Val Ser Val Ala His Asp Ala Ser Gly Lys
    1760                1765                1770

Arg Val Tyr Tyr Leu Thr Arg Asp Pro Thr Thr Pro Leu Ala Arg
    1775                1780                1785

Ala Ala Trp Glu Thr Ala Arg His Thr Pro Val Asn Ser Trp Leu
    1790                1795                1800

Gly Asn Ile Ile Met Tyr Ala Pro Thr Leu Trp Ala Arg Met Ile
    1805                1810                1815

Leu Met Thr His Phe Phe Ser Ile Leu Leu Ala Gln Glu Gln Leu
    1820                1825                1830

Glu Lys Ala Leu Asp Cys Gln Ile Tyr Gly Ala Cys Tyr Ser Ile
    1835                1840                1845

Glu Pro Leu Asp Leu Pro Gln Ile Ile Gln Arg Leu His Gly Leu
    1850                1855                1860

Ser Ala Phe Ser Leu His Ser Tyr Ser Pro Gly Glu Ile Asn Arg
    1865                1870                1875

Val Ala Ser Cys Leu Arg Lys Leu Gly Val Pro Pro Leu Arg Val
    1880                1885                1890

Trp Arg His Arg Ala Arg Ser Val Arg Ala Arg Leu Leu Ser Gln
```

```
                                -continued
    1895                1900                1905
Gly Gly Arg Ala Ala Thr Cys Gly Lys Tyr Leu Phe Asn Trp Ala
    1910                1915                1920

Val Arg Thr Lys Leu Lys Leu Thr Pro Ile Pro Ala Ala Ser Gln
    1925                1930                1935

Leu Asp Leu Ser Ser Trp Phe Val Ala Gly Tyr Ser Gly Gly Asp
    1940                1945                1950

Ile Tyr His Ser Leu Ser Arg Ala Arg Pro Arg Trp Phe Met Trp
    1955                1960                1965

Cys Leu Leu Leu Leu Ser Val Gly Val Gly Ile Tyr Leu Leu Pro
    1970                1975                1980

Asn Arg
    1985

<210> SEQ ID NO 3
<211> LENGTH: 21
<212> TYPE: DNA
<213> ORGANISM: Artificial
<220> FEATURE:
<223> OTHER INFORMATION: Primers

<400> SEQUENCE: 3
gggagagcca tagtggtctg c                                              21

<210> SEQ ID NO 4
<211> LENGTH: 20
<212> TYPE: DNA
<213> ORGANISM: Artificial
<220> FEATURE:
<223> OTHER INFORMATION: Primers

<400> SEQUENCE: 4
cccaaatctc caggcattga                                                20

<210> SEQ ID NO 5
<211> LENGTH: 21
<212> TYPE: DNA
<213> ORGANISM: Artificial
<220> FEATURE:
<223> OTHER INFORMATION: Probe

<400> SEQUENCE: 5
cggaattgcc aggacgaccg g                                              21
```